United States Patent
Fujii et al.

(10) Patent No.: US 7,632,979 B2
(45) Date of Patent: Dec. 15, 2009

(54) ABSORBING ARTICLE HAVING HONEYCOMB RECESSES ON LOWER ABSORBENT LAYER AND VARYING LAYER DENSITIES

(75) Inventors: Takako Fujii, Tokyo (JP); Satoko Konawa, Tochigi (JP); Masanori Kondo, Tochigi (JP)

(73) Assignee: Daio Paper Corporation, Ehime (JP)

( * ) Notice: Subject to any disclaimer, the term of this patent is extended or adjusted under 35 U.S.C. 154(b) by 136 days.

(21) Appl. No.: 10/675,229

(22) Filed: Sep. 29, 2003

(65) Prior Publication Data

US 2004/0116884 A1 Jun. 17, 2004

(30) Foreign Application Priority Data

Sep. 30, 2002 (JP) ............................. 2002-287231
Mar. 31, 2003 (JP) ............................. 2003-097164

(51) Int. Cl.
*A61F 13/15* (2006.01)
(52) U.S. Cl. ....................... 604/378; 604/379; 604/380; 604/385.101
(58) Field of Classification Search ......... 604/378–380, 604/358, 385.01, 383, 38.101, 385.28; 428/116, 428/98; 128/113.1; 156/89.22
See application file for complete search history.

(56) References Cited

U.S. PATENT DOCUMENTS 3,431,911 A * 3/1969 Meisel, Jr. .................. 604/360
3,468,311 A * 9/1969 Gallagher ................... 604/370
3,667,468 A * 6/1972 Nystrand et al. ............. 604/380
3,707,430 A * 12/1972 Costanza et al. ............. 428/169
3,908,659 A * 9/1975 Wehrmeyer et al. ......... 604/374
4,435,178 A * 3/1984 Fitzgerald ................... 604/365
4,685,915 A * 8/1987 Hasse et al. ................. 604/378
4,738,675 A 4/1988 Buckley et al. ............. 604/380
5,188,624 A * 2/1993 Young et al. ................ 604/378
5,454,800 A * 10/1995 Hirt et al. ................... 604/378
6,287,288 B1 9/2001 Osborn, III et al. ......... 604/385
6,296,628 B1 * 10/2001 Mizutani .................... 604/387
6,586,653 B2 * 7/2003 Graeme et al. .............. 604/375
6,610,904 B1 * 8/2003 Thomas et al. .............. 604/383

FOREIGN PATENT DOCUMENTS

| EP | 0613671 A2 | * | 9/1994 |
| EP | 1219275 A2 | | 7/2002 |
| JP | 57-205503 | | 12/1982 |
| JP | 64-45801 | | 2/1989 |
| JP | 8-503397 | | 4/1996 |
| JP | 2001-170111 | | 6/2001 |

* cited by examiner

Primary Examiner—Jacqueline F. Stephens
(74) Attorney, Agent, or Firm—Ladas & Parry LLP

(57) ABSTRACT

A body fluid absorbing article, which is improved in the spot absorptivity and in the diffusivity in an absorbent, and which is improved in the characteristics of a body fluid migration to the absorbent. The body fluid absorbing article comprises an absorbent sandwiched between a body fluid permeable surface member and a body fluid impermeable back member. Said absorbent includes an upper layer and a lower layer sequentially from the side of said body fluid permeable surface member, and said lower layer has a higher density than that of said upper layer.

13 Claims, 18 Drawing Sheets (a)

(b)

ABSORBING ARTICLE HAVING HONEYCOMB RECESSES ON LOWER ABSORBENT LAYER AND VARYING LAYER DENSITIES

BACKGROUND OF THE INVENTION

1. Field of the Invention

The present invention relates to a body fluid absorbing article such as a sanitary napkin or a paper diaper for absorbing and holding a body fluid and, more particularly, to a body fluid absorbing article having a laminated absorbing structure, which is improved in the spot absorptivity and in the diffusivity in an absorbent, and which is improved in the characteristics of a body fluid migration to the absorbent.

2. Description of the Related Art

As this body fluid absorbing article having the laminated absorbing structure, there is known in the prior art a two-layered structure, as disclosed in JP-A-2001-170111, or a three-layered structure, as disclosed in JP-T-8-503397. The former is cubically bulged by forming an upper layer smaller than a lower layer in the portion of the sanitary napkin to be brought into abutment against the discharge portion of a human body. The latter is provided with three-layer absorbent whose each layer is dense over substantially whole area and is enabled to hold the satisfactory characteristics of the material for sucking the fluid even if the discharge quantity increases.

Generally, the absorbent used in the body fluid absorbing article of this kind is characterized by causing the body fluid to permeate the more quickly for the lower density and the more slowly for the higher density but by holding the body fluid the more easily. The present invention has been conceived by making skillful use of those characteristics. On the contrary, the aforementioned body fluid absorbing article of the prior art has disclosed the laminar structure for the absorbent but has failed to make the layers different in density. Without this view point, moreover, the existing body fluid absorbing article is not excellent in both the spot absorptivity and the body fluid diffusivity.

In the prior art, moreover, it has been disclosed in JP-A-57-205503 or JP-A-64-45801, for example, that the body fluid treating characteristics in the absorbent, that is, the absorptivity and the diffusivity are adjusted to block the flow of the body fluid thereby to prevent the leakage by embossing the absorbent of the body fluid absorbing article.

With the absorbent being thus embossed, the indented portions take a high density, and the remaining portions take a low density. These indented portions (or the higher density portions) and the remaining portions (or the lower density portions) are not in the laminated relation in the thickness direction of the absorbent. No matter how the density might be adjusted, therefore, the absorbing mode can neither absorb the body fluid quickly nor then diffuse it. As a result, the body fluid hardly permeates, and the higher density portions of a high body fluid absorbing and retaining properties come into contact with the surface layer to contact with the skin. Thus, there arise problems that the body fluid flows back (as called the "wet back"), and that the wearer feels a sticky feel. Especially when the indented portions are formed by the embossing treatment or the like on the surface layer side of the absorbent, there arises a problem that the migration of the body fluid to the absorbent is insufficient.

As a countermeasure for preventing a sideway leakage in the body fluid absorbing article, moreover, there is also known a method of increasing the liquid distribution in the longitudinal direction by indenting the absorbing structure from the surface to the back and by forming longitudinally extending indented lines in the two side portions of the body fluid absorbing article. Much body fluid is held in the high density portions to abut against the skin so that the problem of the back flow or the sticky feel becomes more serious than the of the case of JP-A-57-205503 or JP-A-64-45801. Moreover, these methods still have problems that the absorbent structure becomes hard to give an uncomfortable feel to the wearer, and that the cushioning properties are lost to establish a clearance between the absorbing structure and the body of the wearer.

In the body fluid absorbing article of the prior art, as described hereinbefore, the spot absorptivity, i.e., the ability to receive the body fluid quickly in the absorbent, and the diffusivity, i.e., the ability to diffuse the body fluid throughout the inside of the absorbent cannot be said sufficient in the least, although they are extremely important factors from the viewpoints of the using feel and the leakage prevention.

SUMMARY OF THE INVENTION

The present invention has been conceived in view of the background thus far described and has an object to provide a body fluid absorbing article, which is improved in the spot absorptivity and in the diffusivity in an absorbent, and which is improved in the characteristics of a body fluid migration to the absorbent.

The above-specified object of the invention is achieved by providing a body fluid absorbing article comprising an absorbent sandwiched between a body fluid permeable surface member and a body fluid impermeable back member, characterized: in that the absorbent includes an upper layer and a lower layer sequentially from the side of the top sheet; and in that the lower layer has a higher density than that of the upper layer.

Moreover, the above-specified object of the invention is effectively achieved by providing a body fluid absorbing article, which is characterized in that the density of the lower layer is made higher than that of the upper layer by forming indented recesses in the lower layer of the absorbent.

Moreover, the above-specified object of the invention is effectively achieved by providing a body fluid absorbing article, which is characterized in that the absorbent has the indented recesses formed in the body side face of the lower layer.

Moreover, the above-specified object of the invention is effectively achieved by providing a body fluid absorbing article, which is characterized in that the absorbent has the indented recesses formed in the opposite side face of the body side face of the lower layer.

Moreover, the above-specified object of the invention is effectively achieved by providing a body fluid absorbing article, which is characterized in that the contact portion in the absorbent with the body fluid permeable surface member and the contact portion in the body fluid permeable surface member with the absorbent do not have the clearance, which might otherwise be caused by forming the indented recesses.

Moreover, the above-specified object of the invention is effectively achieved by providing a body fluid absorbing article, which is characterized in that the body fluid permeable surface member is either a top sheet to contact with the body or a second sheet sandwiched between the top sheet and the absorbent.

Moreover, the above-specified object of the invention is effectively achieved by providing a body fluid absorbing article, which is characterized in that the absorbent is not provided, at the portion in the upper layer to contact with the lower layer and at the portion in the lower layer to contact with the upper layer, with the clearance, which might otherwise be caused by forming the indented recesses.

Moreover, the above-specified object of the invention is effectively achieved by providing a body fluid absorbing article, which is characterized in that the absorbent is constructed such that at least two side portions of the lower layer are squeezed out from the end portions of the upper layer, and such that the absorbent satisfies relations of B>A and B>C, if the upper layer has a density A, if the portion in the lower layer corresponding to the upper layer has a density B, and if the squeeze-out portion of the lower layer has a density C.

Moreover, the above-specified object of the invention is effectively achieved by providing a body fluid absorbing article, which is characterized in that the density A of the upper layer and the density C of the squeeze-out portion of the lower layer have a relation of C>A.

Moreover, the above-specified object of the invention is effectively achieved by providing a body fluid absorbing article, which is characterized: in that the density A of the upper layer is 20 to 50 Kg/m$^3$; in that the density B of the portion in the lower layer to correspond to the upper layer is 40 to 120 Kg/m$^3$; and in that the density C of the squeeze-out portion of the lower layer is 20 to 80 Kg/m$^3$.

Moreover, the above-specified object of the invention is effectively achieved by providing a body fluid absorbing article, which is characterized: in that the indented recesses are the recesses of the emboss pattern formed by an embossing treatment; and in that the recesses of the emboss pattern have an array, in which the shortest mutual distance is 3 mm or less.

Moreover, the above-specified object of the invention is effectively achieved by providing a body fluid absorbing article, which is characterized in that the indented recesses are formed into a continuous net shape.

Moreover, the above-specified object of the invention is effectively achieved by providing a body fluid absorbing article, which is characterized in that the indented recesses have an emboss percentage of 30 to 55%, as determined as the ratio of the thicknesses before and after an embossing treatment.

Moreover, the above-specified object of the invention is effectively achieved by providing a body fluid absorbing article, which is characterized in that the indented recesses are formed of linear portions having an angle of 45 degrees or less between the inclination direction of the indented recesses and the longitudinal direction of the article.

Moreover, the above-specified object of the invention is effectively achieved by providing a body fluid absorbing article, which is characterized: in that the indented recesses are formed of linear portions having an angle larger than 45 degrees between the inclination direction of the indented recesses and the longitudinal direction of the article; and in that the linear portions of the article in the longitudinal direction are longer than those of the inclination direction.

Moreover, the above-specified object of the invention is more effectively achieved by providing a body fluid absorbing article, which is characterized: in that the indented recesses are formed of linear portions having an angle larger than 45 degrees between the inclination direction of the indented recesses and the longitudinal direction of the article; and in that the linear portions of the article in the longitudinal direction are wider than those of the inclination direction.

BRIEF DESCRIPTION OF THE DRAWINGS

FIG. 4(*b*) is a top plan view of an essential portion showing a specific example of the first indenting treatment.

FIG. 4(*c*) is a top plan view of an essential portion showing a specific example of the first indenting treatment.

FIG. 4(*d*) is a top plan view of an essential portion showing a specific example of the first indenting treatment.

FIG. 5(*b*) is atop plan view of an essential portion showing a specific example of the second indenting treatment.

FIG. 5(*c*) is a top plan view of an essential portion showing a specific example of the second indenting treatment.

FIG. 5(*d*) is a top plan view of an essential portion showing a specific example of the second indenting treatment.

FIG. 6(*b*) is a sectional view of VI-VI of FIG. 6(*a*).

FIG. 8(*b*) is a top plan view of an essential portion showing an example of another preferred indenting treatment.

FIG. 8(*c*) is a top plan view of an essential portion showing an example of another preferred indenting treatment.

FIG. 8(*d*) is a top plan view of an essential portion showing an example of another preferred indenting treatment.

DETAILED DESCRIPTION OF THE PREFERRED EMBODIMENTS

The present invention will be described in detail in connection with its optimum embodiments with reference to the accompanying drawings.

Figure 1:
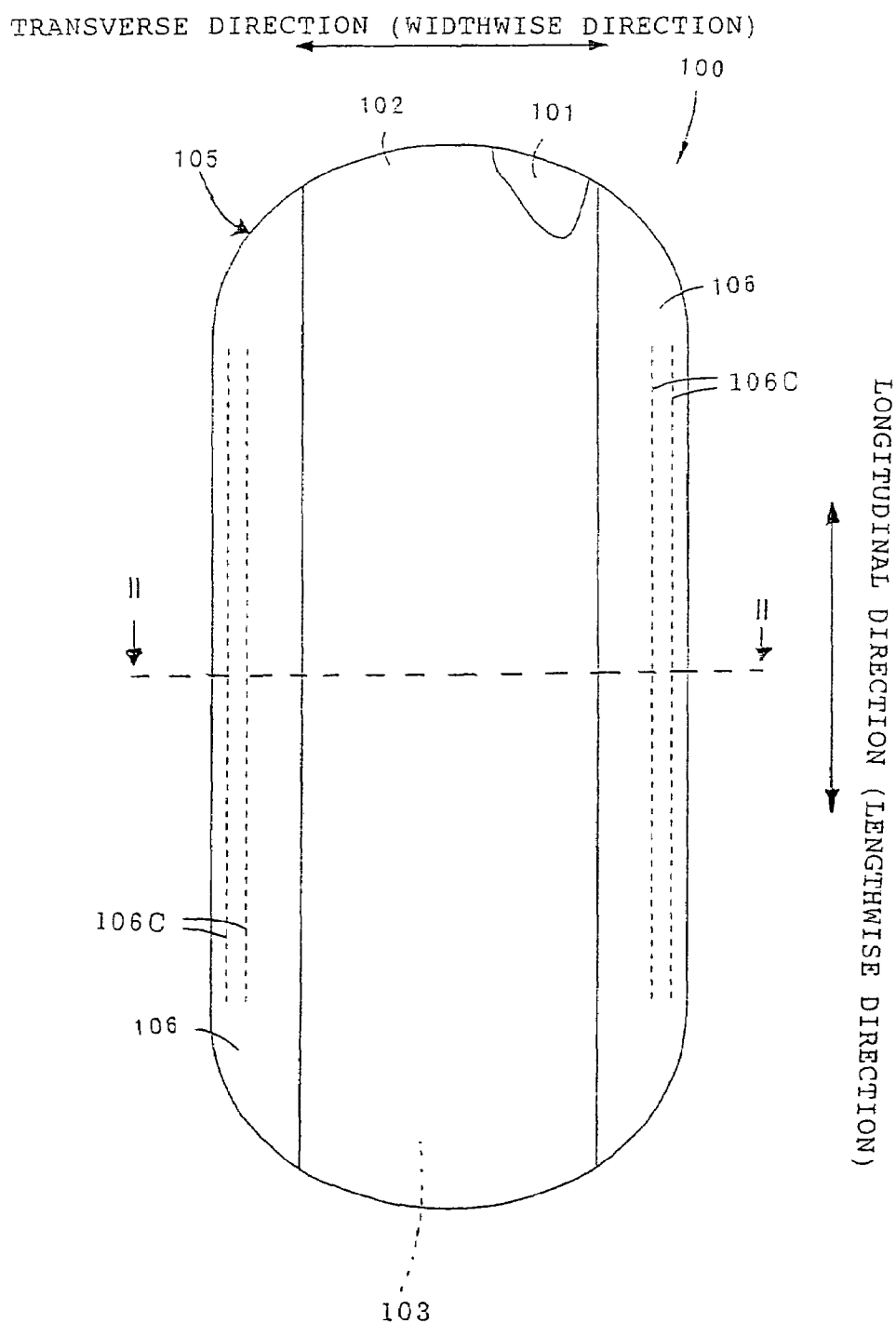
FIG. 1 is a partially broken top plan view of a sanitary napkin according to a first embodiment of the invention.
Figure 2:
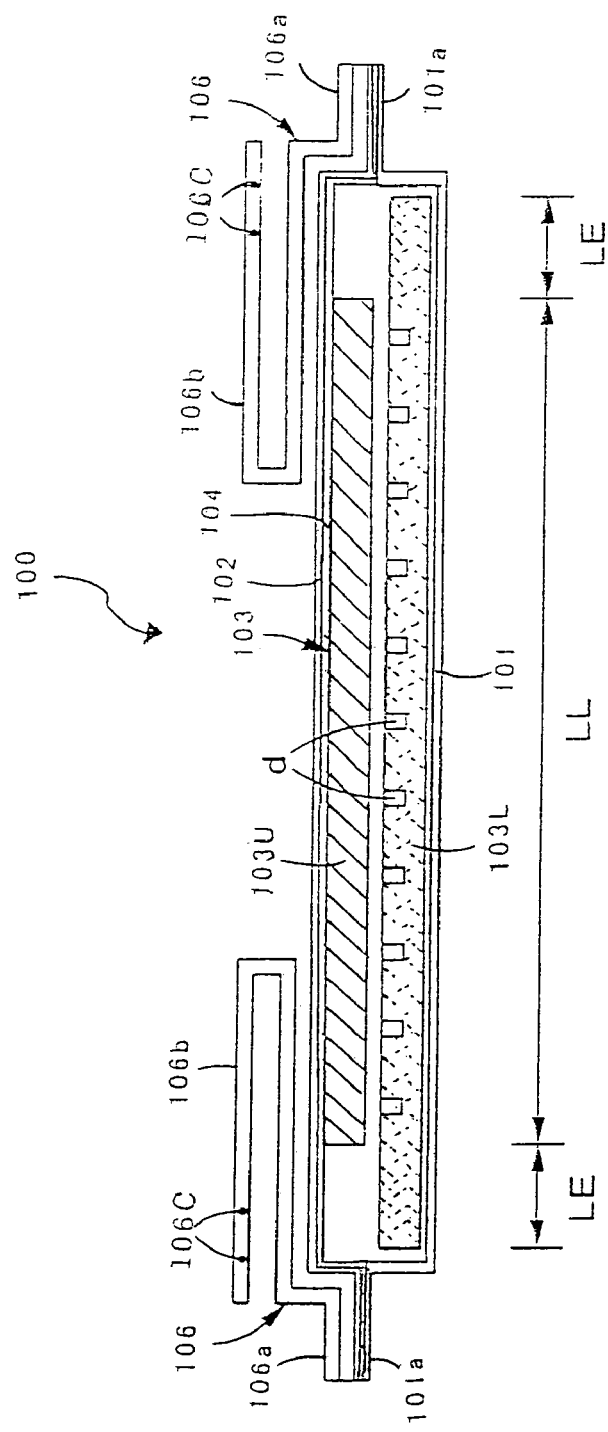
FIG. 2 is a sectional view of II-II of FIG. 1.

FIG. 1 is a partially broken top plan view of a sanitary napkin 100 according to an embodiment of the invention. FIG. 2 is a sectional view of II-II of FIG. 1. Here, the invention should not necessarily be limited to this sanitary napkin 100 but can be applied generally to other body fluid absorbing articles such as various paper diapers.

This sanitary napkin 100 is formed of a body 105, which is composed of: a liquid impermeable back sheet 101 made of a polyethylene sheet, polypropylene sheet or the like; a liquid permeable top sheet 102 for allowing a body fluid such as sanitary blood or discharge (as will be called the "body fluid") to permeate quickly therethrough; an absorbent 103 sandwiched between those sheets 101 and 102 while being covered, if necessary, substantially all over itself with water-absorbent paper such as crepe paper and made of cotton pulp, synthetic pulp or the like; and a second sheet 104 sandwiched between the top sheet 102 and the absorbent 103.

The back sheet 101 constructs a body fluid impermeable backing member. As this material, there is usually used a sheet material having an impermeability, such as an olefin resin sheet of polyethylene or polypropylene allowing no body fluid to permeate therethrough. In addition, there can also be used a laminate nonwoven fabric in which a nonwoven fabric is laminated on a polyethylene sheet or the like as well as a nonwoven fabric sheet (In this case, the back sheet is formed of the water repelling film and a nonwoven fabric. And, there is adopted a lamination mode, in which an outer layer nonwoven fabric is position on the outer face of the product.) retaining the substantial liquid impermeability by interposing a water repelling film. In recent years, moreover, it is a tendency to use a moisture permeable sheet with a view to preventing the stuffiness. This water impermeable/moisture permeable sheet material is exemplified by a porous sheet, which is prepared by blending an inorganic filler into an olefin resin such as polyethylene or polypropylene to form a sheet and by elongating the sheet in a uniaxial direction or biaxial directions.

The top sheet 102 constructs the body fluid permeable surface member together with the later-described second sheet 104. As the material for the top sheet 102, there is suitably used a nonwoven fabric having pores or not or a porous plastic sheet, which can permeate the body fluid therethrough. The material fibers for that nonwoven fabric can be exemplified by not only synthetic fibers of olefin groups such as polyethylene or polypropylene, a polyester group or a polyamide group but also regenerated fibers such rayon or cupra, or natural fibers such as cotton, and by a nonwoven fabric obtained by a suitable processing method such as the spun lace method, the spun bond method, the thermal bond method, melt-blown method or the needle punch method. Of these processing method, the spun lace method is excellent in richness of softness and drape, and the thermal bond method is excellent in bulkiness and softness.

Moreover, the top sheet 102 can be given a surface emboss (although not shown). The surface emboss herein termed is given at a step before the top sheet 102 is combined with the absorbent 103, so that the absorbent 103 is not deformed.

The absorbent 103 can be exemplified by the known one, which is formed of fluffy pulp and a highly absorptive polymer, and maybe covered as a whole, if necessary, with water absorptive paper such as crepe paper. The highly absorptive polymer can not only be mixed as particles, for example, into the pulp constructing the absorbent but also can be held on the surface of the absorbent. As the pulp, moreover, there can be enumerated cellulose fibers of chemical pulp or dissolving pulp made from wood, or artificial cellulose fibers of rayon or acetate. The soft wood pulp having longer fibers is preferred in the function and the price to the hard wood pulp. Here, the absorbent 103 looks flat because it is schematically shown, but is usually formed into a centrally high shape, in which the longitudinal and widthwise centers are bulged from the periphery so as to improve the fitness.

Here in this sanitary napkin 100, the body fluid permeable surface member is constructed sandwiching the second sheet 104 having a higher body fluid penetration rate than the top sheet 102, between the top sheet 102 and the absorbent 103, but the second sheet 104 could be omitted. The second sheet 104, if any, acts as the body fluid permeable layer to contact with the body side face of the absorbent 103. Without the second sheet 104, on the other hand, the top sheet 102 acts as the body fluid permeable layer to contact with the body side face of the absorbent 103. With the second sheet 104 being sandwiched as in this sanitary napkin 100, the body fluid received by the top sheet 102 quickly penetrates into the second sheet 104, so that the wet-back is effectively prevented.

The second sheet 104 used and satisfying that function has a lower fiber density than that of the top sheet 102. On the other hand, the second sheet 104 does not make direct contact with the skin so that it can also be made of a nonwoven fabric of short fibers. Moreover, the second sheet 104 can also be formed of a meshed film or a porous nonwoven fabric. The second sheet 104 may also contain water retaining fibers. These water retaining fibers can be exemplified by fibers of rayon or cellulose derivatives and can be woven into another material. Moreover, a hydrophilic agent can also be added to the second sheet 104. As the material for the nonwoven fabric, there can be enumerated polypropylene, polyethylene, polyethylene terephthalate, polyamide, nylon, rayon, vinylon or acryl. In the case of the direct method, there can be preferably adopted the nonwoven fabric of polypropylene, polyethylene terephthalate or nylon fibers. For the joint of short fibers, on the other hand, the mode of point adhesion with heat or adhesive or interlace with water flow or needle can be enumerated by the wet method, the dry method (e.g., the air lay method or the card method) or the spun lace method. There can also be enumerated a nonwoven fabric, which is formed of complex fibers of a core/shell or side-by-side structure. As these complex fibers, there can be enumerated polyethylene terephthalate/polyethylene, polypropylene/polyethylene or polypropylene/polypropylene.

On the two side portions of the surface side of the present sanitary napkin 100, as shown in FIG. 1, there are provided side nonwoven fabrics 106 and 106, which extended longitudinally along substantially the whole length of the sanitary napkin 100. As shown in FIG. 2, the side nonwoven fabrics 106 and 106 are extended sideways at their portions 106a, and the back sheet 101 is also extended sideways at its portion 101a. The extended sideway portions 106a of the side nonwoven fabrics 106 and the extended sideway portion 101a of the back sheet 101 are jointed to each other with a hot-melt adhesive or the like.

The side nonwoven fabric 106 can be made of a water-repelled nonwoven fabric or a hydrophilically treated nonwoven fabric in accordance with the function stressed. If the function to prevent the penetration of the body fluid or to enhance the skin touch is stressed, for example, there is used the water-repelled nonwoven fabric, which is coated with a water repellent of silicone group, paraffin group or ACC group. If the absorptivity of the body fluid on the two side portions of the surface side is stressed, on the other hand, there is used the hydrophilically treated nonwoven fabric, which is made by swelling or making porous the synthetic fibers by a method of polymerizing it in the presence of the oxidized product of a chemical compound such as polyethylene glycol having a hydrophilic group in the manufacture process of the synthetic fibers or by a method of treating with a metallic salt such as stannic chloride to dissolve the surface partially thereby to make it porous and to deposit the hydroxide of the metal, and which is made hydrophilic by applying the capillarity. For the reasons thus far described, the hydrophilically treated nonwoven fabric is desirably used as the side nonwoven fabrics 106. These side nonwoven fabrics 106 can be made of natural fibers, synthetic fibers or regenerated fibers by a suitable treating method but, preferably, the nonwoven fabric, which is made air-permeable by suppressing the "METSUKE" (or its intended volume).

As shown in FIG. 2, the side nonwoven fabrics 106 have a double structure, the inner side portions 106b of which are extended from the side edge of the absorbent 103 to the widthwise central side (or inward) and are adhered in the double sheet state onto the top sheet 102 with the hot-melt adhesive. The inner side portions 106b are folded back outward from their adhered side edges, and elastically stretchable members 106C and 106C such as rubber threads are adhered in the stretched state to those folded-back portions with the hot-melt adhesive. These folded-back portions of the side nonwoven fabrics 106 are adhered in the superposed state at their longitudinal front and back end portions to each other and to the surface of the top sheet 102 with the hot-melt adhesive but not at their intermediate portions. In the used state, therefore, the longitudinally intermediate portions are raised by the shrinking forces of the elastic stretchable members 106C and 106C so that the raised portions function as sideway leakage preventing barriers (i.e., solid gathers) T and T against the body fluid.

Figure 3:
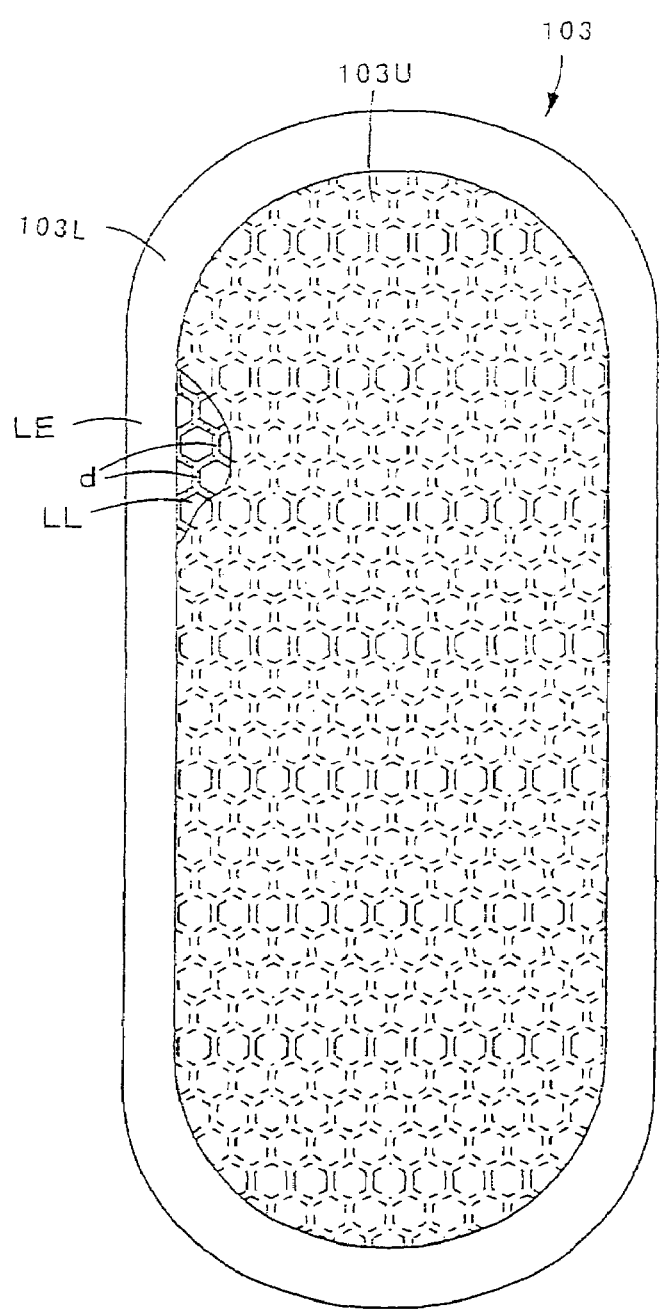
FIG. 3 is a partially broken top plan view of an absorbent.

As shown in the section in FIG. 2 and in the partially broken section of the absorbent in FIG. 3, the absorbent 103 of the present sanitary napkin 100 has a double structure composed of: an upper layer 103U contacting with the top sheet 102; and a lower layer 103L having an upper face adjoining the upper layer 103U and a lower face contacting with the back sheet 101. The density of the lower layer 103L is made higher than that of the upper layer 103U by embossing the body side (or the upper face) of the lower layer 103L to form indented recesses d. In this case, the lower layer 103L and the upper layer 103U may be formed to have identical sizes and shapes, but the lower layer 103L may also be enlarged to squeeze its portions out of the end portion of the upper layer 103U. In the latter case, the denser and harder lower layer 103L forms the edge portions of the absorbent 103 so that the squeeze-out portions undesirably give the angular skin touch to the wearer. In order to solve this problem, on the other hand, the upper layer 103U could squeeze out of the end portions of the lower layer 103L. If the less dense upper layer 103U having a higher body fluid permeability and a lower body fluid retention are squeezed out, however, the wet back or the like may occur at the squeeze-out portions LE.

Therefore, the present embodiment is constructed: such that at least the two side portions (which exert most influences on the aforementioned skin touch because they abut against the inner sides of the thighs) of the lower layer 103L or, preferably, all their peripheral edges are squeezed out of the end portions of the upper layer 103U; and such that the relations of B>A and B>C are satisfied, if the upper layer 103U has a density A, if a portion LL of the lower layer 103L, as corresponding to the upper layer 103U, has a density B and if the squeeze-out portions LE of the lower layer 103L have a density C. As a result, those squeeze-out portions LE of the lower layer 103L, which have a lower density than the higher density portion of the lower layer 103L, form the peripheral edge portions of the absorbent 103 so that the skin touch is improved.

If this case has the relation of the density C>the density A, that is, the relations of the density B>the density C>the density A, moreover, the body fluid absorbed by the lower layer 103L does not flow back to the upper layer 103U, but it is especially preferred that the body fluid easily diffuses to the squeeze-out portions LE. In order to make these density relations, the upper layer 103U and the lower layer 103L can be laminated by forming the upper layer 103U of the density A, by forming the lower layer 103L of the density C and by embossing or wholly indenting the lower layer portion superposed on the upper layer 103U to indent to the density B.

In the general sanitary napkin, it is recommended that the density A of the upper layer 103U is set at 20 to 50 Kg/m$^3$, preferably at 25 to 40 Kg/m$^3$, and that the density B of the portion LL of the lower layer 103L corresponding to the upper layer 103U is set at 40 to 120 Kg/m$^3$, preferably at 60 to 100 Kg/m$^3$. It is also recommended that the density C of the squeeze-out portions LE of the lower layer 103L is set at 20 to 80 Kg/m$^3$, preferably at 25 to 60 Kg/m$^3$. If the aforementioned density relations are set within those ranges, it is possible to improve the spot absorptivity and the body fluid diffusivity and the skin touch of the peripheral edge portion of the absorbent 103 and to prevent the back flow of the body fluid.

In case the predetermined portion of the lower layer 103L, i.e., the corresponding portion LL of the lower layer 103L to the upper layer 103U in the this embodiment is to be indented, on the other hand, the following four kinds of modes can be taken, as shown in essential top plan views in FIG. 4(a) to 4(d), for example.

In the mode of the first indenting treatment, the indented recesses d are continuous in a net shape. Here, letter p designates the embossed lands, which are not indented. Examples of this first indenting treatment are described in detail. That is: a lattice-shaped emboss pattern (FIG. 4(a)), in which the indented recesses d are continued in groove shapes in the longitudinal direction (or in the longitudinal direction of the absorbent 103) and in the widthwise direction (perpendicular to the aforementioned longitudinal direction) of the napkin body 105; an oblique lattice-shaped emboss pattern (FIG. 4(b)), in which the indented recesses d are continued in groove shapes and inclined with respect to the longitudinal direction; a honeycomb emboss pattern (FIG. 4(c)), in which the indented recesses d are continued in groove shapes and in a honeycomb shape (having the hexagonal embossed lands p); and an emboss pattern (FIG. 4(d)), in which circular the embossed lands p are spaced and arrayed to form a continuous net-shaped indented recess d between them.

In the mode of a second indenting treatment, as shown in essential top plan views in FIGS. 5(a) to 5(d), the indented recesses d and d forming the emboss patterns are spaced and arrayed in the longitudinal direction of the napkin body 105. In short, this mode is formed by reversing the indented recesses d and the embossed lands p, i.e., the aforementioned continuous net-shaped emboss patterns shown in FIGS. 4(a) to 4(d). That is: a lattice-shaped emboss pattern (FIG. 5(a)), in which the embossed lands p are continued in groove shapes in the longitudinal direction and in the widthwise direction of the napkin body 105; an oblique lattice-shaped emboss pattern (FIG. 5(b)), in which the embossed lands p are continued in groove shapes and inclined with respect to the longitudinal direction; a honeycomb emboss pattern (FIG. 5(c)), in which the embossed lands p are continued in groove shapes and in a honeycomb shape (having the hexagonal indented recesses d); and an emboss pattern (FIG. 5(d)), in which the circular indented recesses dare spaced and arrayed to form a continuous net-shaped embossed lands p.

In the mode of a third indenting treatment, as shown in a top plan view in FIG. 6(a) and in a sectional view of VI-VI of FIG. 6(a) in FIG. 6(b), a predetermined portion such as the whole region (i.e., the whole region of the essential portion excepting the peripheral edge portion of the absorbent 103) of the portion LL, as corresponding to the upper layer 103U, of the lower layer 103L is indented flat to form the indented recess d.

Figure 7:
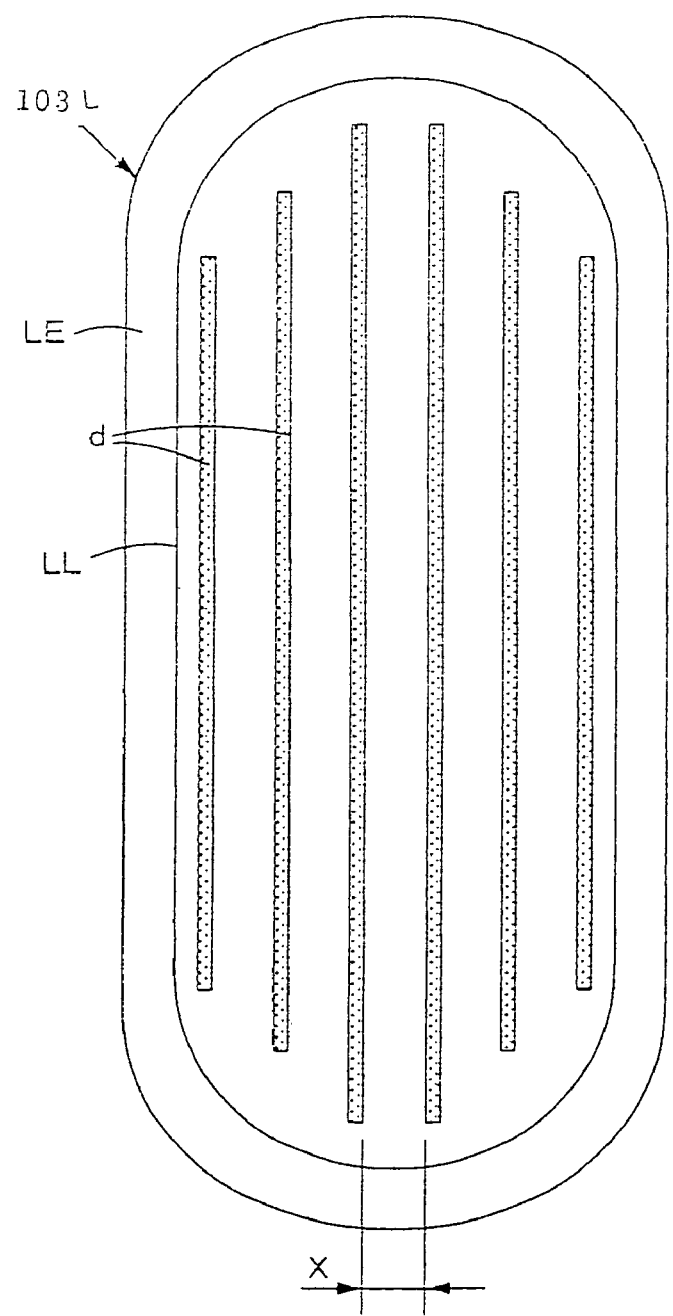
FIG. 7 is a top plan view showing a specific example of a fourth indenting treatment.

In the mode of a fourth indenting treatment, as shown in FIG. 7, there is adopted the emboss pattern, in which a plurality of rows of linear indented recesses d, d, - - -, and so on are continued in parallel with each other in a predetermined direction such as in the longitudinal direction of the napkin body 105.

In this invention, the indentation percentage (as defined as the ratio of the thicknesses before and after the indentation) of the indented recesses d is basically arbitrary. However, it has been found out that the two characteristics of the spot absorptivity and the body fluid diffusivity are satisfactory so long as the indentation percentage is within a range of 30 to 55%. In the indenting treatment of this invention, moreover, the area percentage (i.e., the area of the indented recesses/(the area of the portion to be worked)×100) of the indented recesses d can be arbitrarily set within a range of 20 to 100%, and the range of 30 to 70% is especially suitable. On the other hand, the indented recesses d are preferred to be arrayed all over the absorbent 103, but could be formed only at a portion, e.g., at the central portion involving the body fluid receiving portion.

Here in this invention, for adjusting density, any of the foregoing first to fourth indenting treatment examples can be adopted, but the first indenting treatment example is especially preferable. In the absorbent 103 of the invention, more specifically, the body fluid diffuses along the high-density portion, through which the body fluid hardly permeates. If the indented recesses d corresponding to that high-density portion has the continuous net shape, therefore, the body fluid having reached the lower layer 103L of the absorbent 103 homogeneously diffuses in the net shape or over a wide range, and the high-density portion is continuous without any interruption, so that the body fluid can diffuse remarkably easily.

Even in the emboss patterns of the second and fourth indenting treatment examples, moreover, if there is adopted the proximity array of the shortest mutual spacing X of the indented recesses d, in which the shortest width X (as referred to FIG. 5) of the embossed lands p is 3 mm or less, the body fluid passes through the upper layer 103U of the absorbent 103 over a wider range and reaches the lower layer. From the viewpoint of the aforementioned diffusivity, therefore, the indented recesses d are as if they were substantially continuous. However, the diffusivity is naturally improved more prominently with the continuous net shape, as in the foregoing first indenting treatment example.

Figure 4:
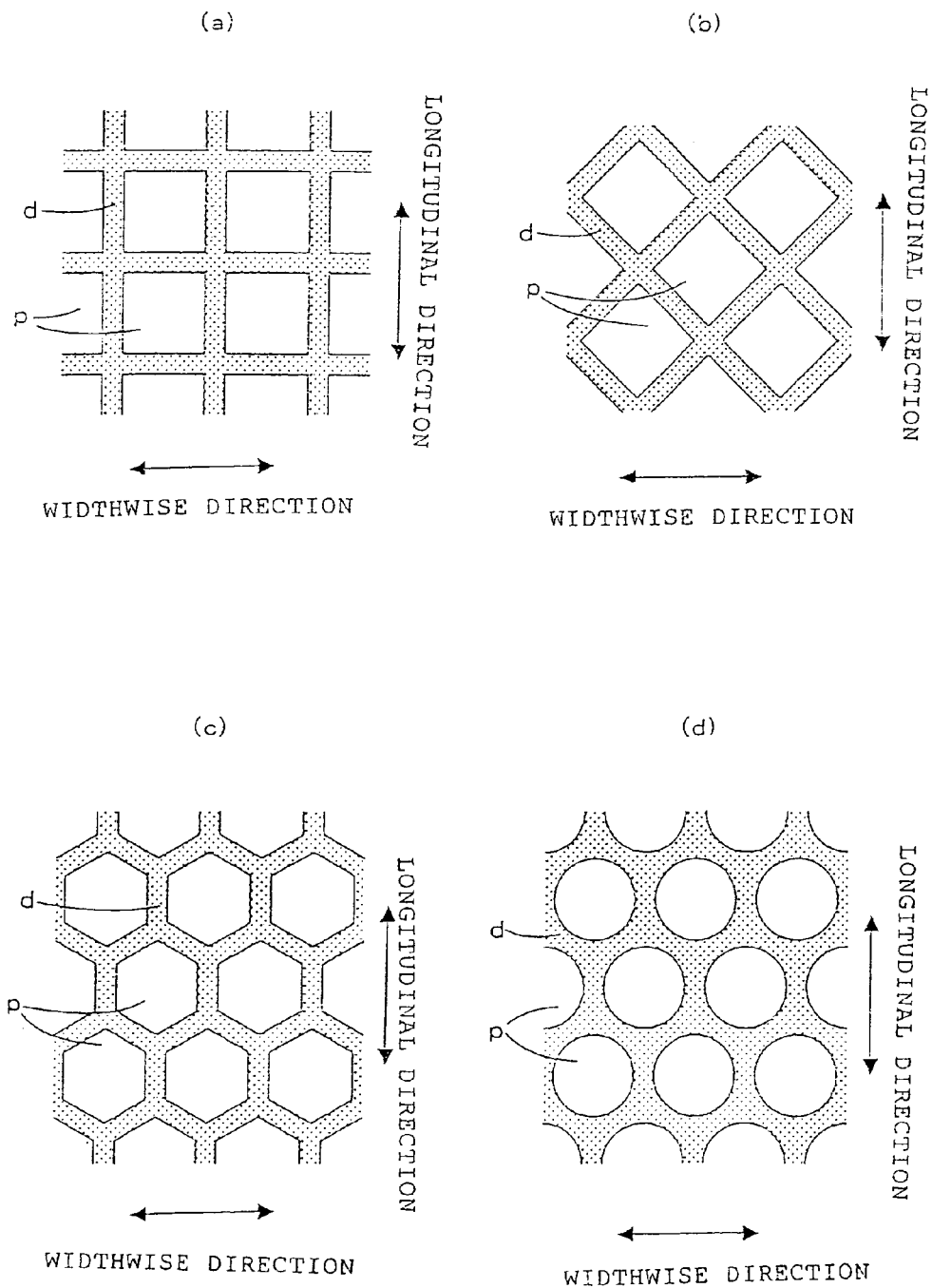
FIG. 4(*a*) is a top plan view of an essential portion showing a specific example of a first indenting treatment.
Figure 5:
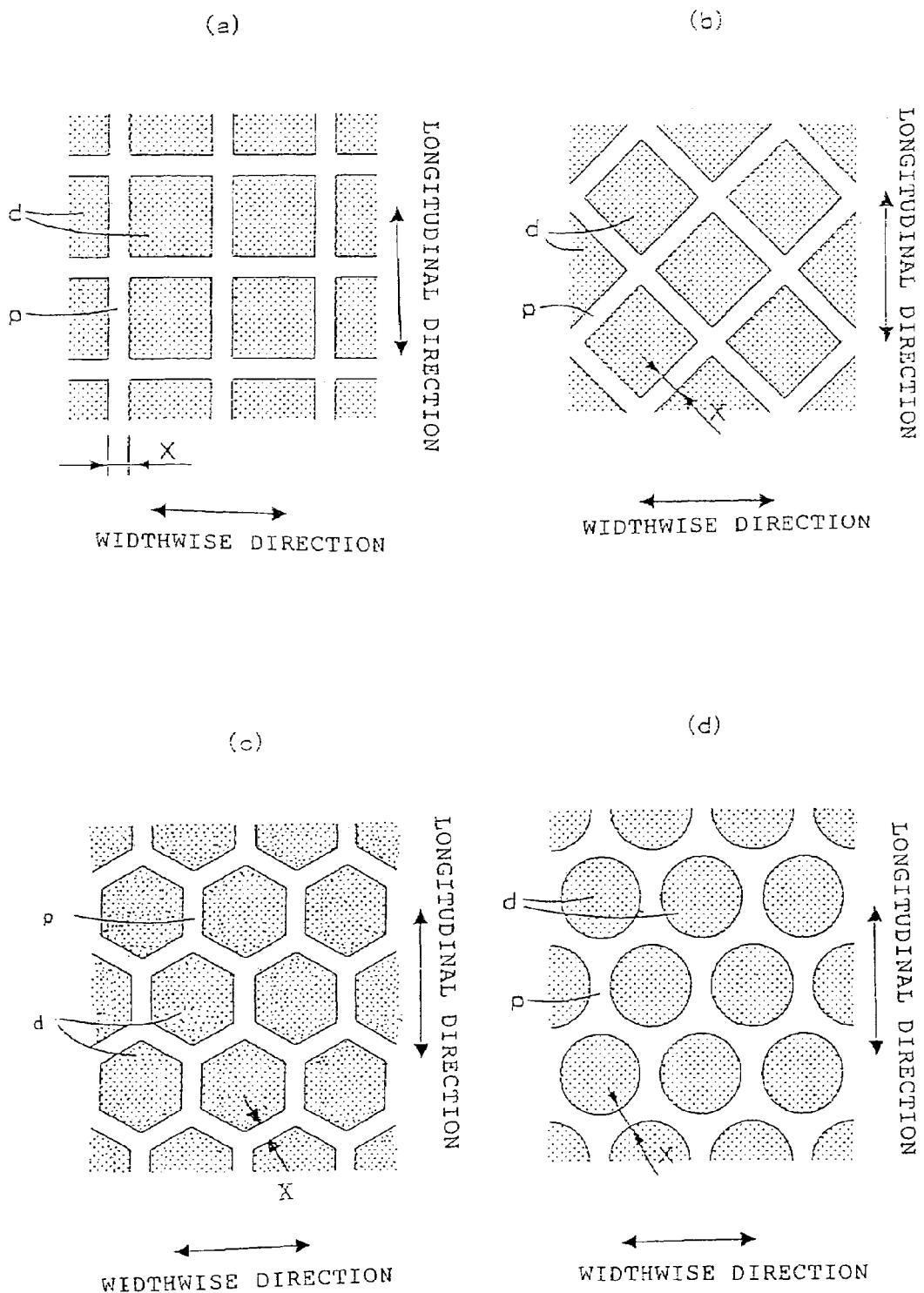
FIG. 5(*a*) is a top plan view of an essential portion showing a specific example of a second indenting treatment.

Especially in case the body fluid diffusivity in the longitudinal direction of the napkin body 105 is stressed, it is preferred that the angle a made between the direction of inclination of the indented recesses d and the longitudinal direction of the napkin body 105 is 45 degrees or less, as shown in FIGS. 8(a) and 8(b). In the example shown in FIG. 8(a), the angle of inclination of the example shown in FIG. 4(c) is changed. In the example shown in FIG. 8(b), the angle of inclination of the example shown in FIG. 4(b) is changed. The body fluid having reached the lower layer 103L of the absorbent 103 migrates along the indented recesses d, as has been described hereinbefore. By adopting the emboss patterns of the aforementioned angles, therefore, the diffusion of the body fluid in the widthwise direction of the napkin body 105 is suppressed, and the body fluid diffusion in the longitudinal direction is promoted so that the so-called "sideway leakage" hardly occurs.

In order to exhibit similar effects, moreover, in the emboss pattern in which an angle β made between the linear indented recesses d1 in the longitudinal direction of the napkin body 105 and the indented recesses d2 in the inclination direction is larger than 45 degrees (that is, in which those indented recesses d1 and d2 form the net-shaped emboss pattern), as shown in FIG. 8(c), the length E of the indented recesses d1 can be made larger than the length F of the indented recesses d2. In this case, the linear indented recesses d1 for promoting the diffusion of the body fluid in the longitudinal direction take a larger occupation ratio so that they can efficiently diffuse the body fluid having migrated from the upper layer 103U to the lower layer 103L, efficiently in the longitudinal direction of the napkin body 105.

In a similar emboss pattern, that is, the emboss pattern, in which the angle β made between the linear indented recesses d1 in the longitudinal direction of the napkin body 105 and the indented recesses d2 in the inclination direction is larger than 45 degrees, as shown in FIG. 8(d), it is also preferred to make the width W1 of the indented recesses d1 is made larger than the width W2 of the indented recesses d2. In this case, the width W1 of the indented recesses d1 for promoting the diffusion of the body fluid in the longitudinal direction becomes larger to make higher the function of the indented recesses d1 to block the body fluid, so that the diffusion of the body fluid in the longitudinal direction is promoted.

Figure 8:
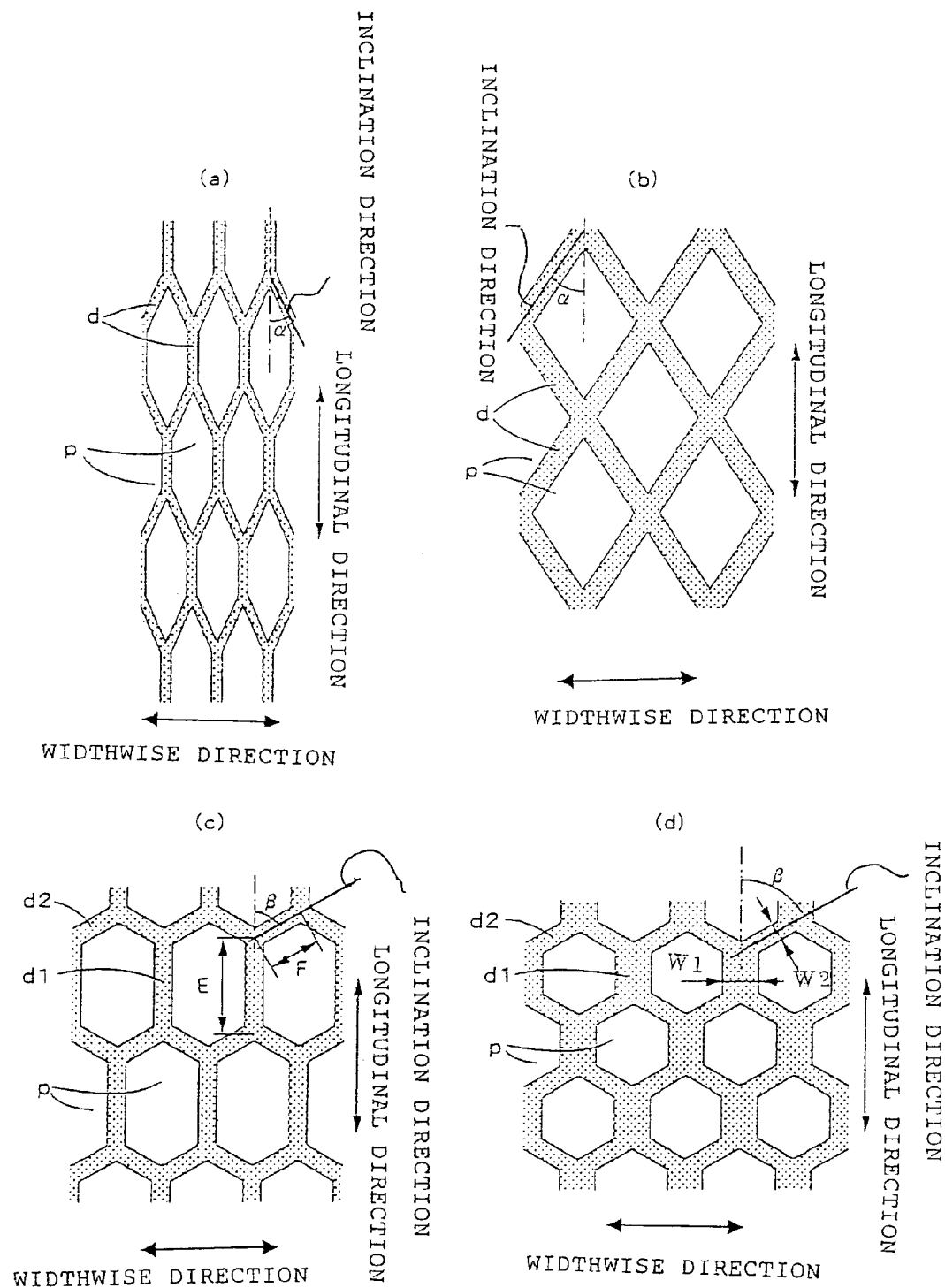
FIG. 8(*a*) is a top plan view of an essential portion showing an example of another preferred indenting treatment.

Here, the mode of FIG. 8(d) can also be combined with the foregoing modes of FIGS. 8(a) and 8(b) and FIG. 8(c). Moreover, these modifications shown in FIG. 8 are based on the first indenting treatment example (i.e., the net-shaped emboss pattern), but could be applied to the patterns of the spaced arrangements of the second indenting treatment example, too, so long as the patterns have the linear indented portions.

Figure 9:
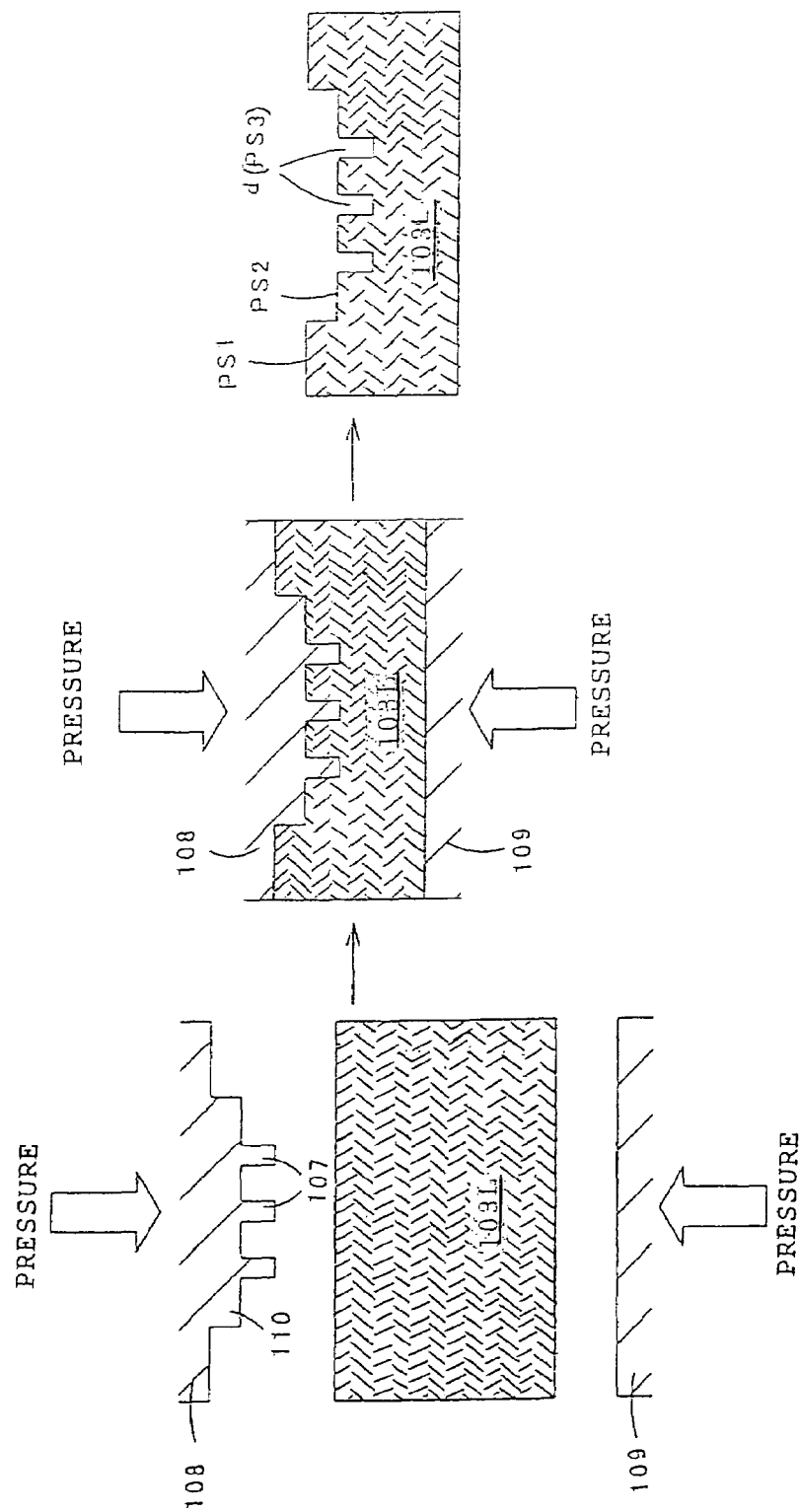
FIG. 9 is a flow diagram of an indenting treatment preferred for the invention.

In the indenting treatment of the absorbent 103 in this embodiment, the lower layer 103L of the absorbent 103 is indented, as shown in FIG. 9, for example, between an emboss roll 108 having a number of indenting ridges 107 on its outer circumference and an anvil roll 109 having no ridge on its outer circumference, thereby to form corrugations on the body side face of the lower layer 103L. After this, the upper layer 103U prepared independently and that lower layer 103L are laminated to manufacture the absorbent 103.

In this embodiment, moreover, a radially enlarged portion 110 is formed on the widthwise intermediate portion of the emboss roll 108, and the indenting ridges 107 are formed on the outer circumference of that radially enlarged portion 110, as shown in FIG. 9. Thus, the indenting treatment can also be done by forming a first indented portion PS1 with the two widthwise end portions of the emboss roll 108, by forming a second more indented portion PS2 with the radially enlarged portion 110, and by forming third still more indented portions PS3 than the second indented portions PS2 with the indenting ridges 107.

As apparent from the forgoing description, the density adjustment of the absorbent 103 of this embodiment can be done not only by the indenting treatment such as the embossing treatment but also by indenting the absorbent 103 in its entirety at the times of forming the individual layers 103U and 103L after the pulp making step.

Here, the first embodiment thus far described is directed to the sanitary napkin 100, in which the indented recesses d are formed in the body side upper face of the lower layer 103L of the absorbent 103. Despite of this description, however, the body fluid absorbing article according to this invention should not be limited to the aforementioned one but can be modified in construction, as follows.

Here will be described a sanitary napkin 100(A) or a body fluid absorbing article according to a second embodiment of the present invention. This sanitary napkin 100(A) is substantially identical in construction to the foregoing sanitary napkin 100 but for the construction of the indented recesses d. In the following, therefore, the construction components corresponding to those of the aforementioned sanitary napkin 100 will be described by attaching the symbol (A) to their reference numerals.

Figure 10:
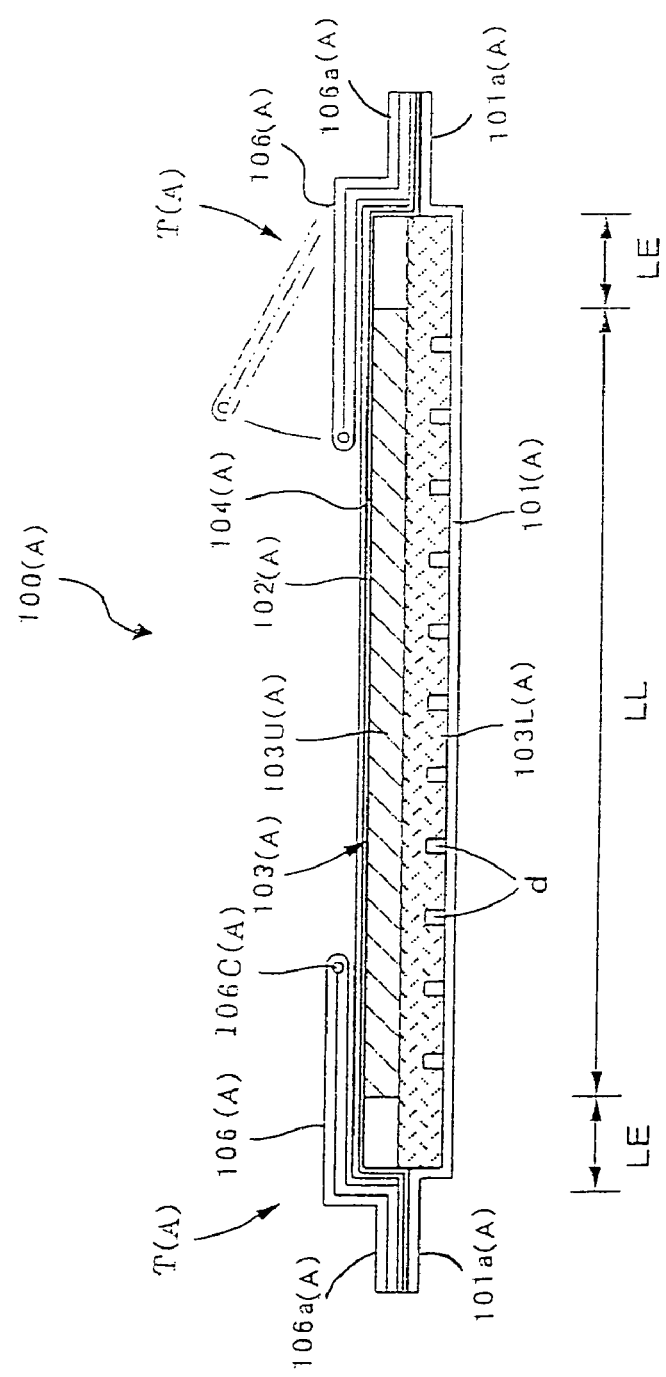
FIG. 10 is a sectional view of a sanitary napkin according to a second embodiment of the invention.

The applied portion of the present embodiment is shown in section in FIG. 10, as in FIG. 2. Specifically, the sanitary napkin 100(A) according to this embodiment is formed of a napkin body 105(A), which is composed of: a back sheet 101(A); a top sheet 102(A); an absorbent 103(A) sandwiched between those sheets 101(A) and 102(A) while being covered, if necessary, substantially all over itself with water-absorbent paper such as crepe paper; and a second sheet 104(A) sandwiched between the top sheet 102(A) and the absorbent 103(A).

The absorbent 103(A) of this sanitary napkin 100(A) has a double structure of an upper layer 103U(A) and a lower layer 103L(A) as in the aforementioned sanitary napkin 100. The side face (or the body side face) of the top sheet 102(A) of the lower layer 103L(A) is flattened to have no indented recess d, but the side face (or the opposite side face of the body side) of the back sheet 101(A) is indented by the indenting treatment such as the embossing treatment to form the indented recesses d so that the density of the lower layer 103L(A) is made denser than the upper layer 103U(A).

In this sanitary napkin 100(A), more specifically, the side face (or the opposite side face of the body side face) of the back sheet 101(A) of the lower layer 103L(A) of the absorbent 103(A) is indented by the indenting treatment such as the embossing treatment to form the indented recesses d so as to give the desired body fluid absorbing characteristics and the diffusion characteristics, as shown in FIG. 10. On the contrary, the side face (or the body side face) of the top sheet 102(A) is left flat without irregularities generated by the indenting treatment. In this absorbent 103(A), therefore, the second sheet 104(A) having flat upper and lower faces is held in close contact with the side face of the top sheet 102(A) without any clearance, and the top sheet 102(A) is also held in close contact with the upper face of the second sheet 104(A) without any clearance. Therefore, the body fluid discharged from the body migrates through the wide contacting face of the top sheet 102(A) to the second sheet 104(A) and then to the upper layer 103U(A) of the absorbent 103(A) through the wide contacting face of the second sheet 104(A). After this, the body fluid migrates to the lower layer 103L(A) through the wide contacting face of the upper layer 103U(A). In this sanitary napkin 100(A), more specifically, the body fluid discharged from the body migrates between the members (i.e., between the top sheet 102(A) and the second sheet 104(A)) through the wide contacting faces, and reaches the absorbent 103(A). Between the upper and lower layers 103U(A) and 103L(A) in the absorbent 103(A), moreover, the body fluid migrates through the wide contacting faces. While giving the absorbent 103(A) the desired body fluid absorbing characteristics and diffusion characteristics by the indenting treatment such as the embossing treatment, therefore, the body fluid characteristics to migrate to the absorbent 103(A) are not obstructed by that indenting treatment. Here are omitted the specific constructions of the indented recesses d, because they are identical to those of the aforementioned first embodiment.

Figure 11:
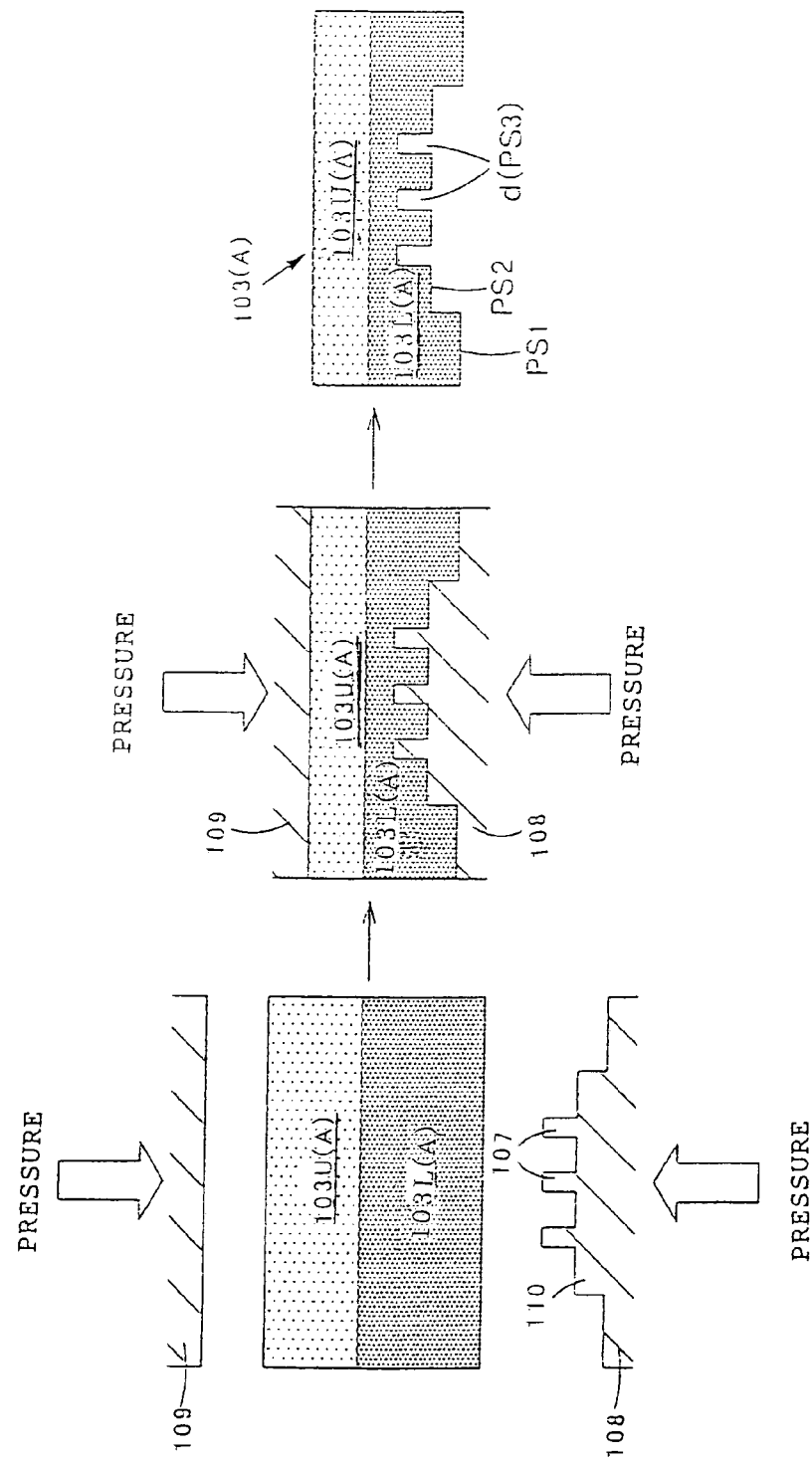
FIG. 11 is a flow diagram of an indenting treatment preferred for the second embodiment of the invention.

In the case of forming the absorbent 103(A), as in the example of this sanitary napkin 100(A), which is composed of the upper layer 103U(A) and the denser lower layer 103L(A), in which the indented recesses d are formed in the side face of the back sheet 101(A) of the lower layer 103L(A), and in which the upper face and lower face of the upper layer 103U(A) and the upper face of the lower layer 103L(A) are made flat, on the other hand, the upper layer 103U(A) and the lower layer 103L(A) may be laminated after they were individually formed, as in the foregoing sanitary napkin 100. In case the indented density adjustment of the upper layer 103U(A) is done at the manufacturing time, however, both the upper layer 103U(A) and the lower layer 103L(A) may be handled together, as shown in FIG. 11, so that the indenting treatment can be done only from the side of the back sheet 101(A) of the lower layer 103L(A).

Here, the foregoing first and second embodiments have been described on the case, in which the body fluid absorbing articles are the sanitary napkins 100 and 100(A). However, the body fluid absorbing article according to the invention should not be limited to the sanitary napkin but can be likewise applied to the paper diaper of tape-type or drawers-type.

Therefore, a body fluid absorbing article according to a third embodiment of the invention will be described on the case, in which it is a paper diaper.

Figure 12:
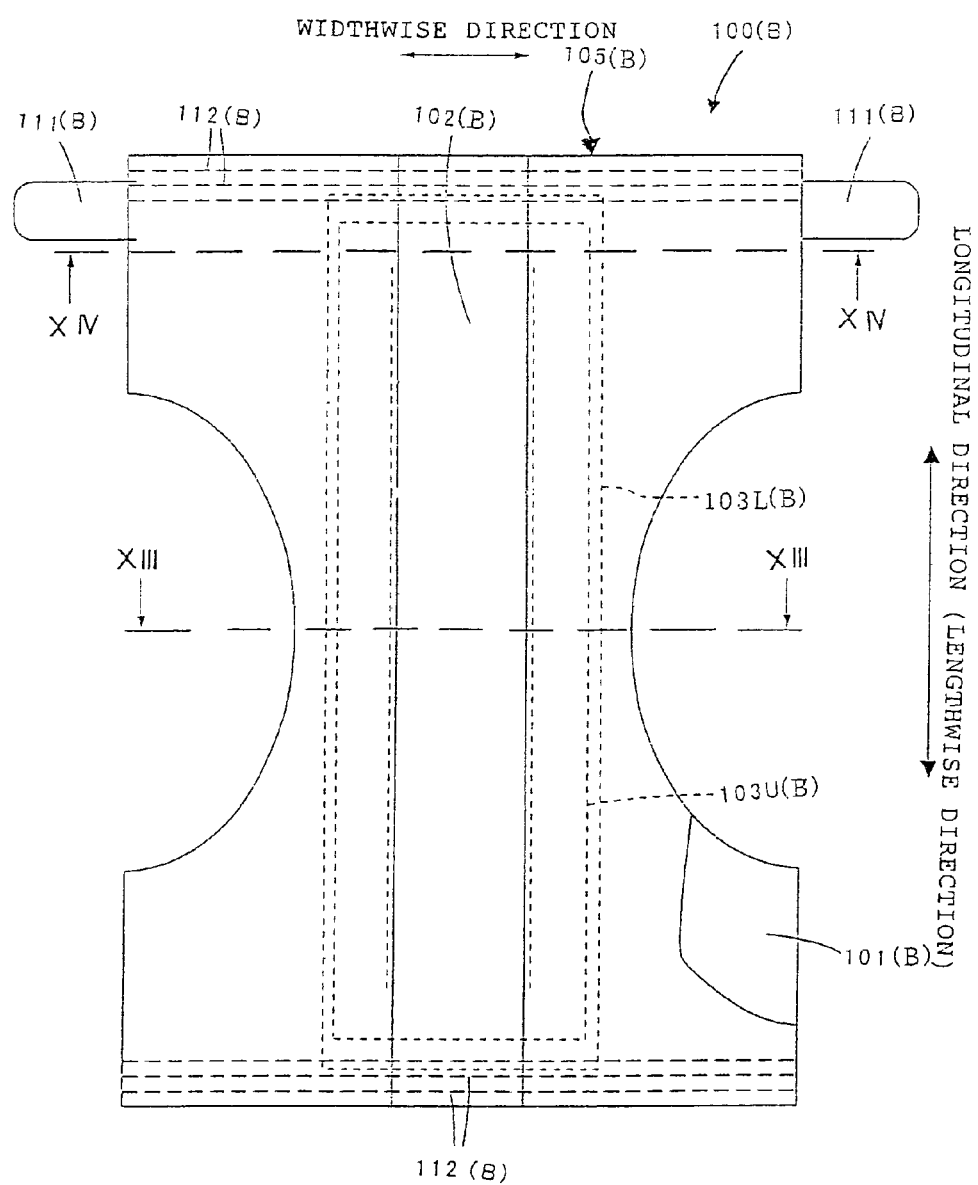
FIG. 12 is a partially broken top plan view of a tape-type paper diaper according to a third embodiment of the invention.
Figure 13:
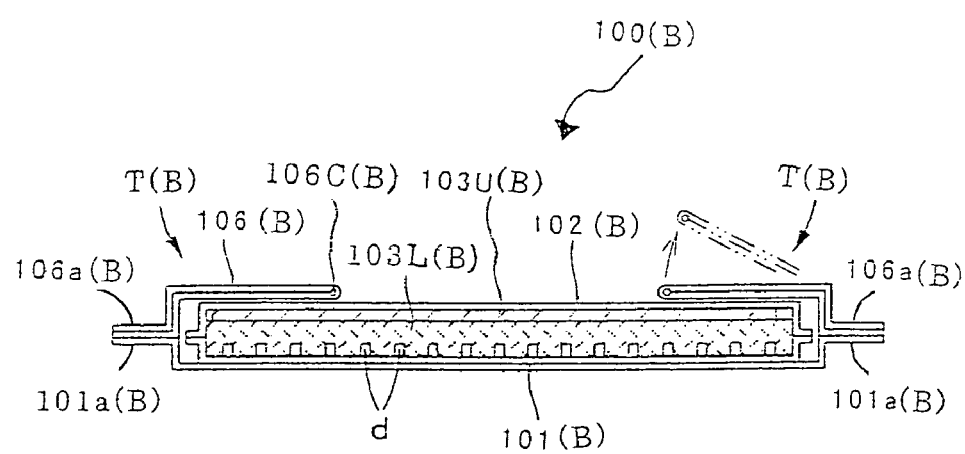
FIG. 13 is a sectional view of XIII-XIII of FIG. 12.
Figure 14:
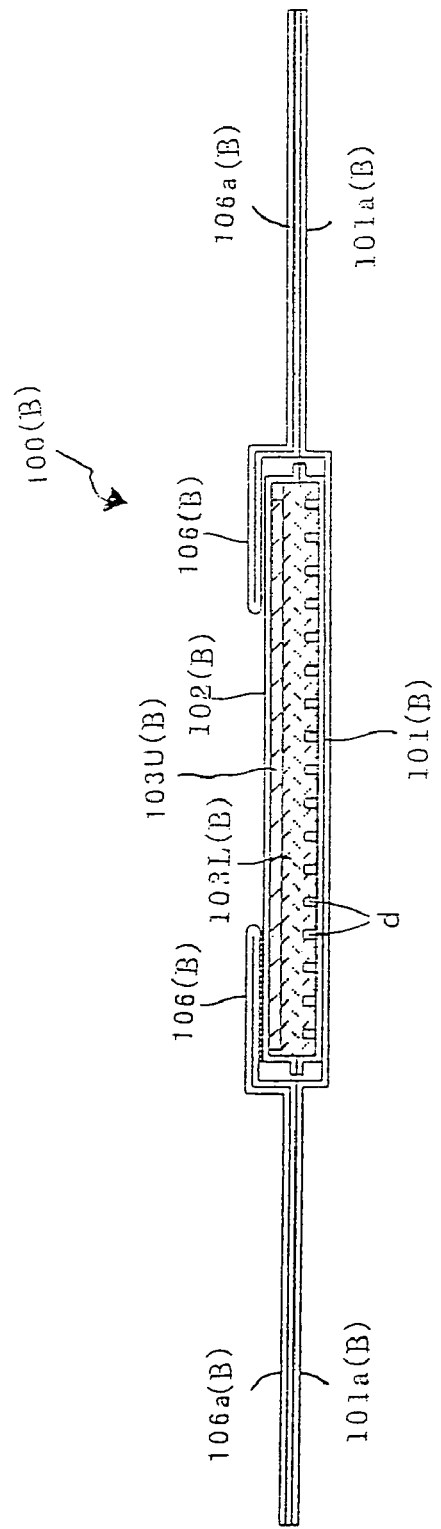
FIG. 14 is a sectional view of XIV-XIV of FIG. 12.

FIG. 12 is a partially broken top plan view of a tape-type paper diaper according to the third embodiment of the invention. FIG. 13 is a sectional view of XIII-XIII of FIG. 12. FIG. 14 is a sectional view of XIV-XIV of FIG. 12. The present tape-type paper diaper 100(B) has its diaper body 105(B) composed of: a back sheet 101(B); a flat top sheet 102(B) for allowing the body fluid such as urine to permeate therethrough; and an absorbent 103(B) sandwiched between the back sheet 101(B) and the top sheet 102(B) for absorbing and holding the body fluid. The paper diaper 100(B) is formed generally into a pseudo sandglass shape, and is provided on its back side with fastening tapes 111(B) for holding the paper diaper body 105(B) in close contact with the body and elastically stretchable members 112(B) made of rubber threads, and on its abdomen side with elastically stretchable members 112(B).

The sideway leakage preventing barriers T(B), as composed of the back sheet 101(B), the top sheet 102(B), the absorbent 103(B) and side nonwoven fabrics 106(B) are substantially identical to those of the foregoing sanitary napkins 100 and 100(A). Therefore, the common construction components will be described by attaching the symbol (B) to their reference numerals. Here, this tape-type paper diaper 100(B) is not provided with a second sheet 104(B), which could also be presented, as in the foregoing sanitary napkins 100 and 100(A).

Moreover, the absorbent 103(B) of this tape-type paper diaper 100(B) is similar to the aforementioned sanitary napkin 100(A) according to the second embodiment, as shown in FIG. 10. In order to give the desired body fluid absorbing characteristics and diffusion characteristics, the side face (or the opposite side face of the body side face) of the back sheet 101(B) of the lower layer 103L(B) is indented by the indenting treatment such as the embossing treatment to form the indented recesses d, but the side face (or the body side face) of the top sheet 102(B) is not treated to form a flat face having no corrugation.

Figure 15:
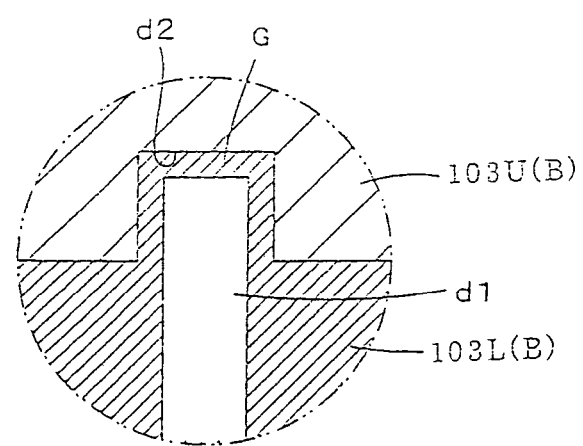
FIG. 15 is a sectional view of an essential portion showing an example of another preferred indenting treatment.

Here in the first to third embodiments thus far described, the indenting treatment such as the embossing treatment is applied only to the lower layer 103L, but can also be applied to the upper layer 103U so long as the magnitude relations of the density of the invention are satisfied. As shown in an essential sectional view in FIG. 15, for example, it is possible to form the indented recess d1, which extends from the side of the back sheet 101(B) of the lower layer 103L(B) into an upper layer 103U(B). In the mode of this case, the close contact is not attained by the contact between the flat faces of the upper and lower layers 103U(B) and 103L(B) of the foregoing examples. However, the indented recesses d2 are also formed in the side face of the upper layer 103U(B) on the side of the lower layer 103L(B). At the same time, the indented recess d2 of the lower layer 103L(B) forms a ridge G, which protrudes in the side face of the upper layer 103U(B), and is fitted in the indented recess d1 of the upper layer 103U(B). This structure enhances the integrity between the upper layer 103U(B) and the lower layer 103L(B) thereby to form none of the clearance, which might otherwise be formed between the upper layer 103U(B) and the lower layer 103L(B) by the indenting treatment. Moreover, the contact area between the upper layer 103U(B) and the lower layer 103L(B) can be made wider than those of the foregoing modes so that the body fluid having reached the inside of the upper layer 103U(B) can migrate more easily to the lower layer 103L(B) through the wider contacting faces.

The body fluid absorbing article according to the present invention has been described in detail on the case, in which it is exemplified by the sanitary napkin and the tape-type paper diaper. However, the body fluid absorbing article according to the invention should not always be limited to the aforementioned sanitary napkin or the tape-type paper diaper but can be properly applied not only to paper diapers for adults and sanitary napkins for a long use or for nights but also generally to the body fluid absorbing articles such as paper diapers for infants, sanitary napkins for daytimes or liner sheets. Moreover, the invention is characterized in the structure of the absorbent so that it can also be applied to the paper diapers of the drawers type and the sanitary napkins of both the blade type having flaps on the side portions or the non-blade type. Especially, this blade type sanitary napkin is provided in its flaps with the absorbents, to which the invention may also be applied.

EXAMPLES (Experiment 1)

A variety of absorbent samples having the double layer structure, in which the upper layer and the lower layer (which are made of fibrous pulp) were made different in the density gradient (i.e., the lower layer density/the upper layer density) in the thickness direction, were manufactured, and the migration feasibility (or the spot absorptivity) of the body fluid from the upper layer to the lower layer was evaluated. The specific procedure will be described in the following.
(1) The various absorbent samples were prepared with upper layers having constant the aforementioned METSUKE and thickness but with lower layers having different densities.
(2) 3 cc of horse blood was naturally dripped from a cylinder, and the diffusion area after 30 seconds was measured.
(3) After 3 minutes, the horse blood was likewise naturally dripped, and the diffusion area after 30 seconds was measured.
(4) After 10 minutes, the weight of the upper layer was measured.

Figure 16:
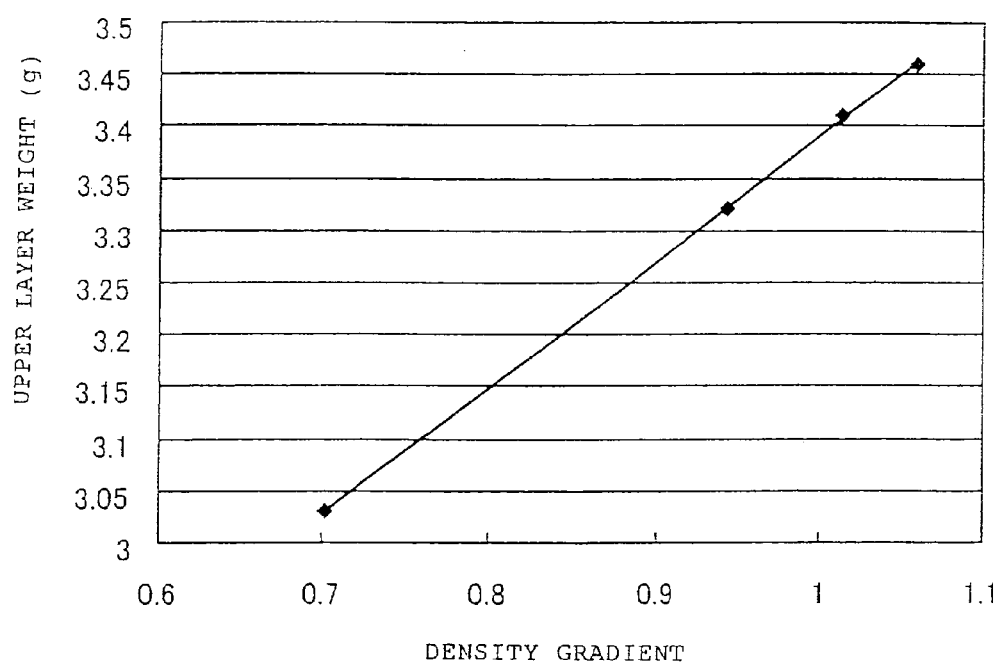
FIG. 16 is a graph plotting a correlation between a density gradient and an upper layer absorption (in weight).

The kinds of samples and the measurement results are enumerated in Table 1. Moreover, a correlation between the density gradient and the upper layer absorption is plotted in FIG. 16. From this result, too, it is found out that the spot absorptivity and the diffusivity can be improved by making the absorbent of the structure having the upper layer and the lower layer and by making the density of the lower layer higher than that of the upper layer.

(Experiment 2)

A variety of absorbent samples, in which the lower layer made of fibrous pulp was given an emboss pattern, were manufactured, and the spot absorptivity and the diffusivity were evaluated. The specific procedure is as follows.
(1) An emboss plate was laid on the lower layer to give an emboss pattern under the conditions common among the individual examples. Moreover, the thickness before and after the embossing treatment were measured to determine the emboss percentage (=the thickness after the emboss/the thickness before the emboss×100). Although natural, the density was the higher for the smaller emboss percentage.
(2) The upper layer was laid on the embossed lower layer. At this time, the weights of the upper layer and the lower layer were measured.
(3) About 0.85 g of horse blood was dripped three times after every one minute through a glass tube having a diameter of 5 mm. After left for 10 minutes, the lower layer diffusion area was measured. Here, this lower layer diffusion area was calculated on the basis of the measured values of the longer axis and the shorter axis by approximating the diffusion area into an elliptic shape.
(4) Moreover, the feasibility of migration of the blood to the lower layer was determined from the following Formula:

Migration Feasibility (%)=Increased Weight of Lower Layer/(Increased Weight of Upper Layer+Increased Weight of Lower Layer)×100.

Figure 17:
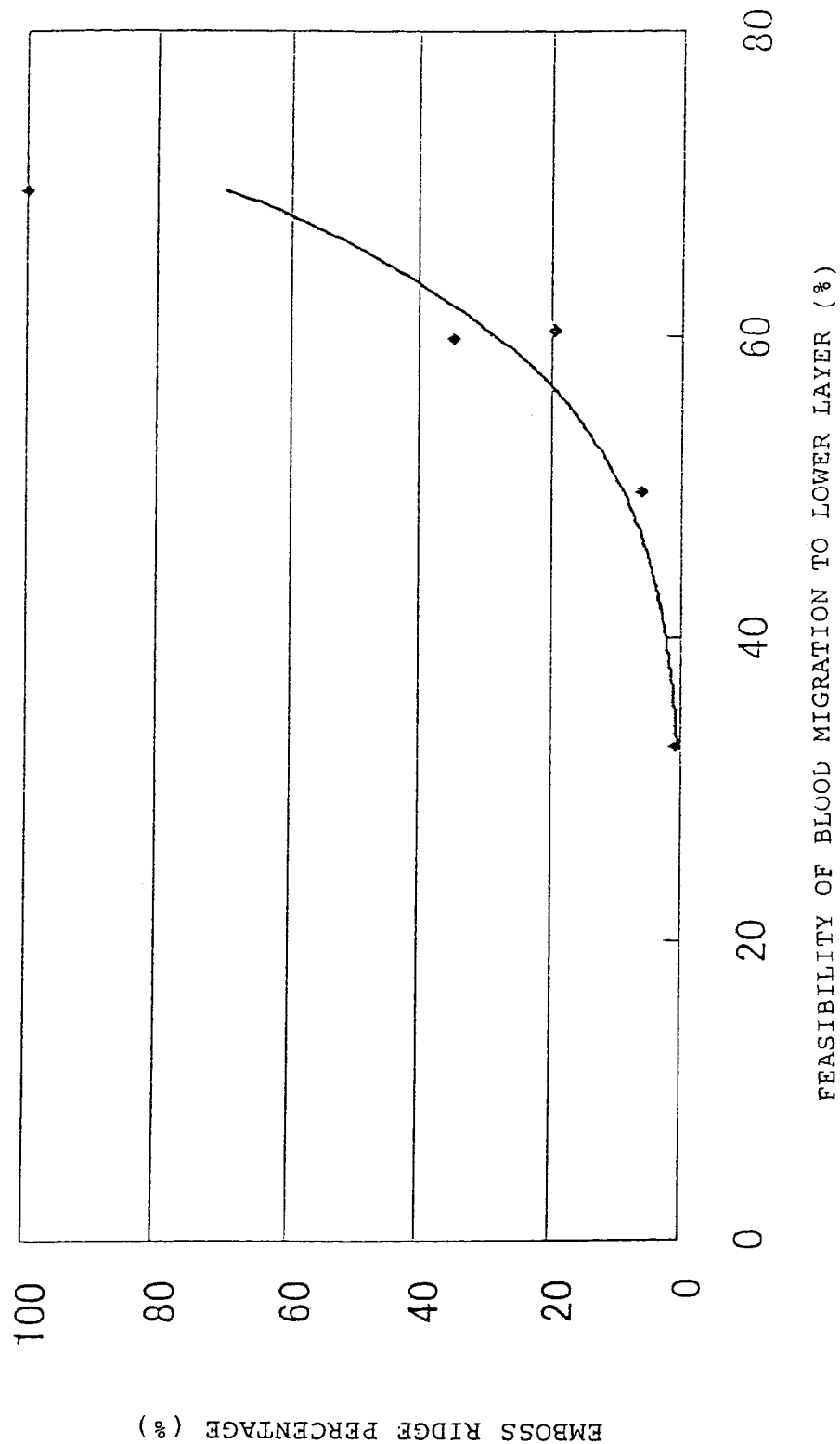
FIG. 17 is a graph plotting a relation between an emboss percentage and a blood migration to a lower layer.
Figure 18:
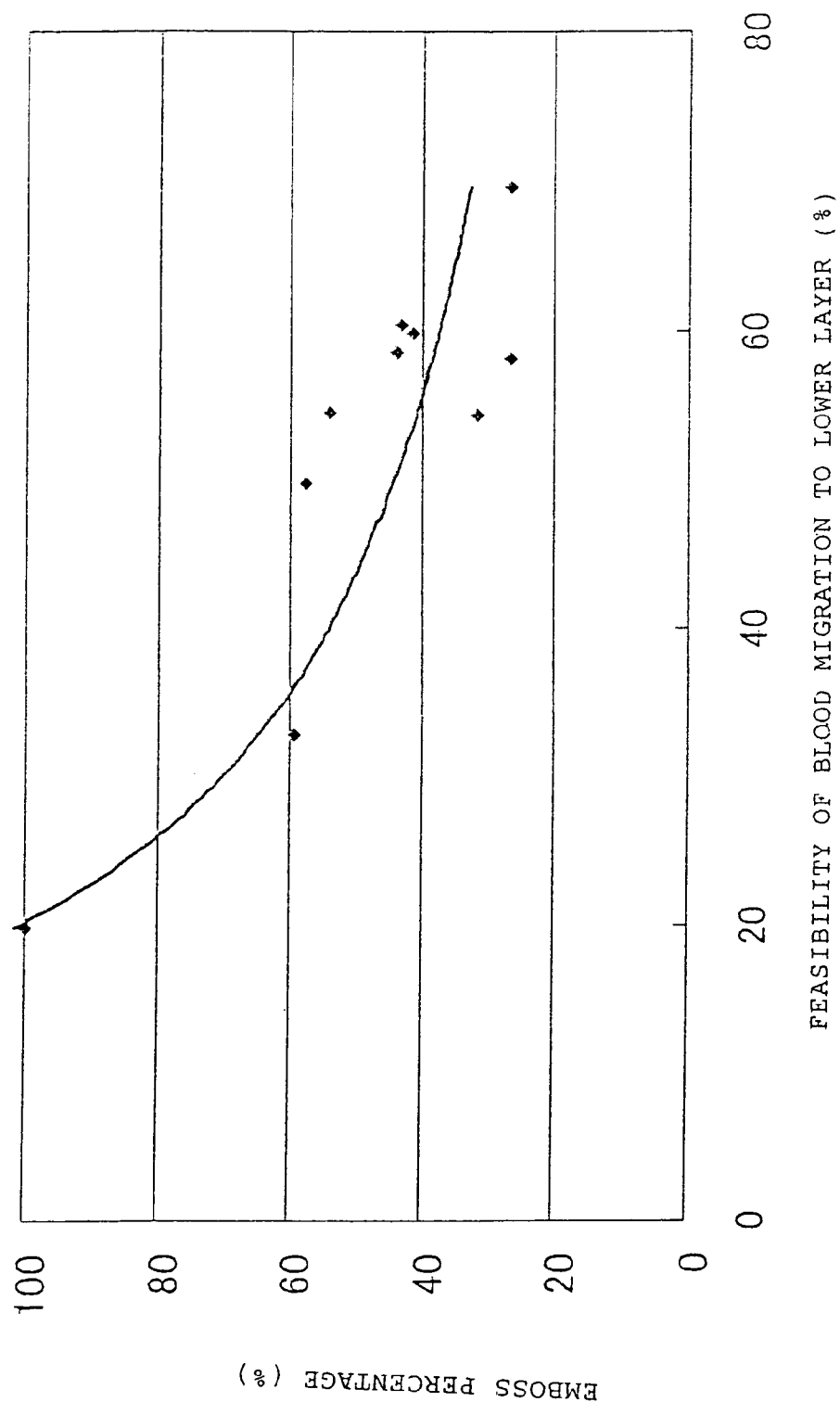
FIG. 18 is a graph plotting a relation between an indentation percentage and a blood migration to a lower layer.

The kinds and measured results of the samples are enumerated in Table 2. Moreover, the relation between the embossed ridge percentage and the feasibility of migration of the blood to the lower layer, and the relation between the emboss percentage and the feasibility of migration of the blood to the lower layer were plotted in FIG. 17 and FIG. 18, respectively.

The following items are found out from the results of Experiment 2.
(i) The indentation has a tendency to become the deeper for the larger emboss ridge percentage, and the blood migrates the more easily to the lower layer as the indentation is the deeper.
(ii) As the migration of the blood to the lower layer is the more feasible, the more blood is absorbed between the upper layer and the lower layer.
(iii) For the smaller emboss height and the shorter inter-emboss distance, the indentation becomes the easier so that the blood easily migrates to the lower layer.
(iv) In the pattern (e.g., the emboss H) having an inter-emboss distance of 0, much blood diffuses along the embosses.
(v) For causing 50% or more of blood to migrate from the upper layer to the lower layer and to diffuse deeply into the lower layer, it is necessary that the emboss percentage is 55% or less and that the inter-emboss distance is 0.

TABLE 1

| Upper Layer | Pulp METSUKE | 320 g/m$^2$ | 320 g/m$^2$ | 320 g/m$^2$ | 320 g/m$^2$ |
|---|---|---|---|---|---|
| | Pulp Thickness | 7.450 mm | 7.450 mm | 7.450 mm | 7.450 mm |
| | Pulp Density | 43.0 kg/m$^2$ | 43.0 kg/m$^2$ | 43.0 kg/m$^2$ | 43.0 kg/m$^2$ |
| Lower Layer | Pulp METSUKE (Containing Polymer) | 285 g/m$^2$ | 285 g/m$^2$ | 285 g/m$^2$ | 285 g/m$^2$ |
| | PulpThickness (Containing Polymer) | 3.918 mm | 5.518 mm | 6.718 mm | 7.018 mm |
| | Pulp Density (Containing Polymer) | 61.3 kg/m$^2$ | 45.6 kg/m$^2$ | 42.4 kg/m$^2$ | 40.6 kg/m$^2$ |
| Density Gradient (Lower Layer Density/Upper Layer Density) | | 1.059 | 1.014 | 0.943 | 0.701 |
| Diffusion Area | 1st | 18.36 cm$^2$ | 11.54 cm$^2$ | 8.47 cm$^2$ | 8.52 cm$^2$ |
| | 2nd | 23.55 cm$^2$ | 17.49 cm$^2$ | 13.50 cm$^2$ | 15.87 cm$^2$ |
| Upper Layer Weight after Absorption | | 3.03 g | 3.32 g | 3.41 g | 3.46 g |

TABLE 2

Figure 6:
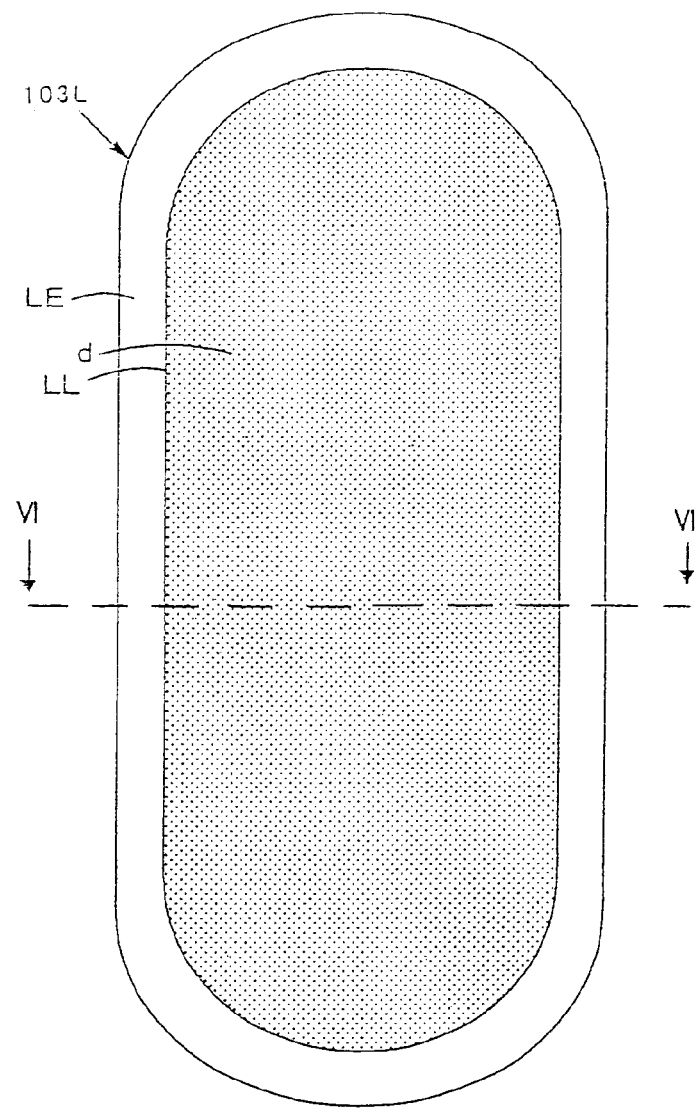
FIG. 6(*a*) is a top plan view of an essential portion showing a specific example of a third indenting treatment.
Figure 6:
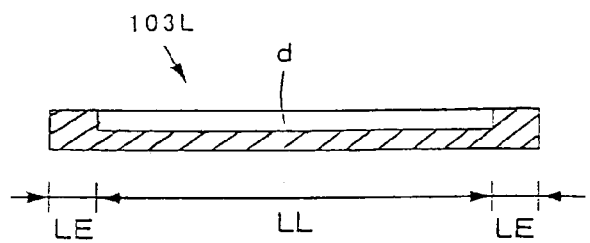

| | No Emboss | Emboss A | Emboss B | Emboss C | Emboss D | Flat | Emboss E | Emboss F | Emboss G | Emboss H |
|---|---|---|---|---|---|---|---|---|---|---|
| Emboss Recess Mode | — | FIG. 5(b) | FIG. 5(b) | FIG. 5(b) | FIG. 4(c) | FIG. 6 | FIG. 5(b) | FIG. 5(c) | FIG. 5(a) | Honeycomb Shape |
| Emboss Ridge Percentage (%) | — | 0.9 | 6.3 | 19.6 | 34.9 | 100 | 19.9 | 24.7 | 51 | 19.6 |
| Inter-Emboss Distance (mm) | — | 7 | 6 | 2 | 2 | 0 | 1 | 2 | 2 | 0 |
| Emboss Height (Depth) (mm) | 2 | 2 | 2 | 2 | 2 | 0 | 2 | 1 | 1 | 1 |
| Emboss Percentage (%) | 100 | 59.4 | 57.7 | 43.1 | 41.6 | 26.8 | 31.8 | 44 | 26.7 | 54 |
| Feasibility of Migration to Lower Layer (%) | 19.9 | 32.8 | 49.7 | 60.5 | 59.9 | 69.7 | 54.3 | 58.6 | 58.1 | 54.5 |
| Diffusion Area of Lower Layer* (mm$^2$) | 470 | 1425 | 3663 | 5495 | 3663 | 2035 | 5414 | 5617 | 4331 | 7327 |

*Lower Diffusion Area: Calculated from the measured values of the longer axis and the shorter axis by approximating the diffusion area into an elliptic shape.

What is claimed is:

1. A body fluid absorbing article comprising:
an absorbent sandwiched between a body fluid permeable surface member and a body fluid impermeable back member,
wherein said absorbent includes an upper layer and a lower layer disposed between said body fluid permeable surface member and said body fluid impermeable back member;
wherein said lower layer has a higher density than that of said upper layer by forming indented recesses in the lower layer of said absorbent that underlies said upper layer into a continuous honeycomb shape;
wherein said indented recesses are formed in linear portions having an angle of 45 degrees or less between an inclination direction of said indented recesses and a longitudinal direction of the article;
wherein said indented recesses have an emboss percentage of 30 to 55%, as determined by the ratio of the thicknesses before and after an embossing treatment;
wherein said lower layer extends beyond an outer edge of said upper layer; and
wherein said absorbent has relations of B>C>A, when said upper layer has a density A, a portion of said lower layer that underlies the upper layer has a density B, and the remaining portion of said lower layer that extends beyond the outer edge of said upper layer has a density C;
wherein the density A is 20 to 50 Kg/m$^3$, the density B is 40 to 120 Kg/m$^3$; and the density C is 20 to 60 Kg/m$^3$;
wherein the shortest mutual distance of said indented recesses is 3 mm or less.

2. A body fluid absorbing article as set forth in claim 1, wherein said indented recesses are formed in a body side face of said lower layer.

3. A body fluid absorbing article as set forth in claim 1, wherein said indented recesses are formed in an opposite side face of body side face of said lower layer.

4. A body fluid absorbing article as set forth in claim 1, wherein both a contact portion with said body fluid permeable surface member in said absorbent and a contact portion with said absorbent in said body fluid permeable surface member do not have a clearance, which might otherwise be caused by forming said indented recesses.

5. A body fluid absorbing article as set forth in claim 1, wherein said body fluid permeable surface member is either a top sheet contacting with a body, or said top sheet and a second sheet sandwiched between said top sheet and said absorbent.

6. A body fluid absorbing article as set forth in claim 1, wherein both a contact portion with said lower layer in said upper layer and a contact portion with said upper layer in said lower layer do not have any clearance, which might otherwise be caused by forming said indented recesses.

7. A body fluid absorbing article as set forth in claim 1, wherein said indented recesses that extend from the side of the body fluid impermeable back member of said lower layer into said upper layer are formed in said absorbent.

8. The body fluid absorbing article as set forth in claim 1, wherein said density A is uniform along the entire upper layer, said density B is uniform along the portion of said lower layer that underlies the upper layer, and density C is uniform along the remaining portion of said lower layer that extends beyond the outer edge of said upper layer.

9. A body fluid absorbing article comprising:
an absorbent sandwiched between a body fluid permeable surface member and a body fluid impermeable back member,
wherein said absorbent includes an upper layer and a lower layer disposed between said body fluid permeable surface member and said body fluid impermeable back member;
wherein said lower layer has a higher density than that of said upper layer by forming indented recesses in the lower layer of said absorbent that underlies said upper layer into a continuous honeycomb shape;
wherein said indented recesses are formed in linear portions having an angle of 45 degrees or less between an inclination direction of said indented recesses and a longitudinal direction of the article;

wherein said indented recesses have an emboss percentage of 30 to 55%, as determined by the ratio of the thicknesses before and after an embossing treatment;

wherein said lower layer has a width and a length and said upper layer has a width and a length;

wherein the width of said lower layer is greater than the width of said upper layer; and wherein said absorbent has relations of B>C>A, when said upper layer has a density A, a portion of said lower layer that underlies the upper layer has a density B, and the remaining portion of said lower layer has a density C.

10. The body fluid absorbing article as set forth in claim 9, wherein said density A is uniform along the entire upper layer, said density B is uniform along the portion of said lower layer that underlies the upper layer, and density C is uniform along the remaining portion of said lower layer that extends beyond the outer edge of said upper layer.

11. A body fluid absorbing article comprising:

an absorbent sandwiched between a body fluid permeable surface member and a body fluid impermeable back member, wherein said absorbent includes an upper layer and a lower layer disposed between said body fluid permeable surface member and said body fluid impermeable back member;

wherein said lower layer has a higher density than that of said upper layer;

wherein said lower layer has a width and a length and said upper layer has a width and a length;

wherein the width of said lower layer is greater than the width of said upper layer; and wherein said absorbent has relations of B>A and B>C, when said upper layer has a density A, a portion of said lower layer that underlies the upper layer has a density B, and the remaining portion of said lower layer has a density C.

12. The body fluid absorbing article as set forth in claim 11, wherein said density A is uniform along the entire upper layer, said density B is uniform along the portion of said lower layer that underlies the upper layer, and density C is uniform along the remaining portion of said lower layer that extends beyond the outer edge of said upper layer.

13. A body fluid absorbing article comprising:

an absorbent sandwiched between a body fluid permeable surface member and a body fluid impermeable back member, wherein said absorbent includes an upper layer and a lower layer disposed between said body fluid permeable surface member and said body fluid impermeable back member;

wherein said lower layer has a higher density than that of said upper layer;

wherein said lower layer has a width and a length and said upper layer has a width and a length;

wherein the width of said lower layer is greater than the width of said upper layer; and wherein said absorbent has relations of B>A and B>C, when said upper layer has substantially unvarying density A, a portion of said lower layer that underlies the upper layer has substantially unvarying density B, and the remaining portion of said lower layer has substantially unvarying density C.

* * * * *